(12) United States Patent
Connolly et al.

(10) Patent No.: US 8,663,918 B2
(45) Date of Patent: *Mar. 4, 2014

(54) METHOD AND SYSTEM FOR SAMPLE PREPARATION

(75) Inventors: Dennis M. Connolly, Rochester, NY (US); Charles DeBoer, Ithaca, NY (US); Vera Tannous, Penfield, NY (US); Christopher Kilcoin, Boulder Creek, CA (US); Konstantin Aptekarev, Santa Cruz, CA (US); David B. Bailey, Webster, NY (US); Richard S. Murante, Rochester, NY (US)

(73) Assignee: Integrated Nano-Technologies, Inc., Henrietta, NY (US)

( * ) Notice: Subject to any disclaimer, the term of this patent is extended or adjusted under 35 U.S.C. 154(b) by 325 days.

This patent is subject to a terminal disclaimer.

(21) Appl. No.: 12/785,864

(22) Filed: May 24, 2010

(65) Prior Publication Data

US 2014/0024822 A1    Jan. 23, 2014

Related U.S. Application Data

(60) Provisional application No. 61/180,494, filed on May 22, 2009.

(51) Int. Cl.
*C12Q 1/68* (2006.01)
*G01N 1/00* (2006.01)

(52) U.S. Cl.
USPC .............................. 435/6.1; 366/348; 436/174

(58) Field of Classification Search
None
See application file for complete search history.

(56) References Cited

U.S. PATENT DOCUMENTS

| | | | |
|---|---|---|---|
| 5,558,838 A | 9/1996 | Uffenheimer | |
| 5,610,010 A | 3/1997 | Surzycki et al. | |
| 6,129,828 A | 10/2000 | Sheldon | |
| 6,374,684 B1* | 4/2002 | Dority | 73/864.81 |
| 6,686,195 B1 | 2/2004 | Colin et al. | |
| 7,608,399 B2 | 10/2009 | Reed et al. | |
| 2002/0106686 A1 | 8/2002 | McKernan | |
| 2002/0172949 A1 | 11/2002 | Gautsch | |
| 2004/0157343 A1 | 8/2004 | Sandell | |
| 2005/0115903 A1 | 6/2005 | Halliler-Soulier et al. | |
| 2005/0282202 A1 | 12/2005 | Brolaski | |
| 2006/0177844 A1* | 8/2006 | Ching et al. | 435/6 |
| 2007/0015177 A1 | 1/2007 | Maron et al. | |
| 2007/0092876 A1* | 4/2007 | Xu | 435/6 |
| 2007/0244314 A1* | 10/2007 | Mori | 536/25.41 |
| 2008/0038740 A1 | 2/2008 | Reed et al. | |
| 2008/0102493 A1* | 5/2008 | Ongena et al. | 435/91.1 |

FOREIGN PATENT DOCUMENTS

| | | |
|---|---|---|
| EP | 1388588 A1 | 2/2004 |
| EP | 1992689 A1 | 11/2008 |
| WO | WO9303150 A1 | 2/1993 |
| WO | WO03084976 A1 | 10/2003 |
| WO | WO2006024851 A2 | 3/2006 |
| WO | WO2010065420 | 6/2010 |

OTHER PUBLICATIONS

Zheng et al. "Bioseparation Techniques and Their Applications", in Cseke et al., Handbook of Molecular and Cellular Methods, 2nd ed. (New York, CRC Press, 2004), 25 pages.*
Aldous, J. of Clinical Microbiology, May 2005, vol. 43, No. 5, pp. 2471-2473.
Mann, The application of ultrasound as a rapid method to provide DNA fragments suitable for detection by DNA bio (11 pgs.), 2004.
Quail, DNA: Mechanics breakage, 2005, Encyclopedia of Life sciences, pp. 1-4.
Yang, World Journal of Gastroenterology, May 2008, vol. 14, No. 18, pp. 2872-2876.

* cited by examiner

*Primary Examiner* — Anne Gussow
*Assistant Examiner* — Neil P Hammell
(74) *Attorney, Agent, or Firm* — Hiscock & Barclay, LLP

(57) ABSTRACT

A method for preparing a sample by utilizing a shearing force in the presence of a size stabilizer to break apart the sample to obtain nucleic acid molecules in a usable size range. Once nucleic acid molecules are obtained, magnetic entanglement particles are used to concentrate and clean the nucleic acid molecules for further testing.

19 Claims, 33 Drawing Sheets

Rectangular Configuration

Rectangular

Constant Radial, Variable ID
Configuration

Constant Radial, Variable ID

Variable Radial, Constant ID
Configuration

Variable Radial, Constant ID
Max Disp – .00132 mm
Max Stress- 7.6 psi

Alcohol fraction

1 Minced ear notch
2 Supernatant from minced ear notch
3 Whole ear notch
4 Minced ear notch Nucleic Acid Isolation from Cattle Ear Tissue Yeast
Grass
Blueberry 60 seconds
30 seconds
15 seconds 1. TE (Tris-(hydroxymethyl)aminomethane) with EDTA (ethylene diamine tetra acetic acid)
2. 10mM Tris-(hydroxymethyl)aminomethane
3. 500 mM sodium phosphate
4. 50 mM sodium phosphate
5. 60 mM sodium citrate
6. 3% sodium chloride
R. Reference ladder

METHOD AND SYSTEM FOR SAMPLE PREPARATION

CROSS-REFERENCE TO RELATED APPLICATIONS

This application claims priority from U.S. Provisional Patent Application Ser. No. 61/180,494, filed May 22, 2009, the contents of which are hereby incorporated in their entirety by reference.

GOVERNMENT LICENSE RIGHTS

The U.S. Government has a paid-up license in this invention and the right in limited circumstances to require the patent owner to license others on reasonable terms as provided for by the terms of one or more of the following Grant Award Nos. DMI-0450472 and IIP-0450472 awarded by National Science Foundation, Contract No. W81XWH-07-2-0109 awarded by US Army Medical Research and Material Command, Contract Nos. W911NF-06-1-0238 and W911NF-09-C-0001 awarded by US Army RDECOM ACQ CTR.

FIELD OF THE INVENTION

This invention relates to a method and system for analyzing samples. More particularly, this invention relates to a method for preparing samples by breaking down a sample to obtain nucleic acid molecules within a usable base pair range. The nucleic acid molecules may be manipulated by utilizing magnetic entanglement nanoparticles. In another embodiment the invention relates to a method for concentrating a sample by utilizing magnetic entanglement nanoparticles. An even further embodiment, relates to multi-chamber valves, and more particularly to multi-chamber rotating valves. The invention further relates to a method for transmitting fluids from storage and sample reservoirs to a reaction chamber.

BACKGROUND OF THE INVENTION

There is continuing interest to improve testing methodologies and decrease time demands on clinical laboratories. Particular testing requires that a sample be broken down to extract nucleic acid molecules such as DNA or RNA.

It is estimated that about 30 million molecular diagnostic tests took place in US medical facilities in 2007. This figure is expected to increase to 67 million in 2009. Many, if not all of these assays, could benefit from a rapid sample preparation process that is easy to use, requires no operator intervention, is cost effective and is sensitive to small size samples.

The use of molecular diagnostics and gene sequencing in research and medical diagnostics are rapidly growing. Molecular techniques provide higher levels of specificity and sensitivity than antibody methods, Genetic sequencing allows for the collection of larges amounts of information not previously available. However, sample preparation is a major cost component of running PCR, real-time PCR, gene sequencing analysis and hybridization testing. In addition, it delays test results and limits the ability to run these assays to laboratories with well trained personnel.

Nucleic acid based identification of biological material first requires isolation of the nucleic acid molecules (NAMs) from the sample. In order for a system to effectively and efficiently meet the users needs, a universal sample preparation process is required. Current sample preparation processes are laborious, time consuming and require laboratory capability. To remain universal, the process must be able to handle a wide variety of input materials. This includes, but is not limited to, viruses, spores, organisms, bacteria and medical diagnostic materials, such as blood, tissue, saliva, urine and feces.

Bead beating has been used for years to isolate nucleic acid molecules from samples. Bead beating is the agitation, usually by ultrasound, of micron size glass beads added to the sample. It is a robust approach which is well suited for use with solids like spores or tissue.

Bead beating has several drawbacks. On one hand, if the sample is treated too long, or at too high a power level, only short fragments less than 100 bases long are produced. On the other hand, if the sample is treated to brief, low power agitation, a low yield of nucleic acid is produced, along with a wide range of fragment sizes. When particular size ranges of nucleic acids are needed, gel electrophoresis of the sample is sometimes employed, cutting the gel sections with the correct size ranges out of the finished gel and extracting the nucleic acid fragments from the gel. This process is both slow and tedious.

In running biological and chemical tests it is often desired to obtain a usable size range of nucleic acid molecules and to concentrate and retain the desired analyte. Concentrating the sample can be a difficult process. Traditional methods for concentrating a biological sample include filtering, rinsing, centrifuging and/or reaction chemistry. Often these steps cannot be preformed in a single processing chamber and require the sample to be transferred to other devices or chambers.

Magnetic nanoparticles are particles which are attracted to a magnetic field. By attaching a magnetic nanoparticle to nucleic acid polymers and applying a magnetic field to a sample, the nucleic acid polymers can be moved to a desired location, thereby concentrating a portion of the sample with the nucleic acid polymers. The sample can then be drawn from the concentrated portion yielding a high amount of nucleic acid polymers.

Appling a magnetic field further allows for manipulating the nucleic acid polymer. For example, by holding a nucleic acid polymer steady a rinse can be applied without washing away the nucleic acid polymer.

In an array of different sensors applying a magnetic field allows for positioning the nucleic acid polymer in the vicinity of a desired test area. The nucleic acid polymer can be manipulated to sequentially interact with a plurality of test areas.

Fluid analysis generally requires a series of process steps. Theses process steps generally require that distinct fluids contact a reaction area at different times and in varying secession. Furthermore, each fluid may require different pre-treatment prior to contacting the reaction area such as chemical, optical, thermal, mechanical, magnetic or acoustical pre-treatment steps. A single fluid sample may be subjected to a variety of pre-treatment steps prior to contact with a reaction area such as heating or ultrasonic processing. As the number of fluids and pre-treatment steps increase the fluid delivery system becomes more complex.

Present designs for fluid delivery systems are customized for a particular process and are not easily converted to new processes. Generally, fluid delivery systems comprise a series of chambers uniquely configured for pre-treating and delivering a particular fluid. These systems are not easily adaptable to new pre-treatment steps or fluid delivery without changing both the chambers and delivery procedure.

Therefore, there is a need for a method to prepare nucleic acid samples from any source in a desired size range, rapidly and economically.

Further, a magnetic entanglement particle that specifically binds to target analytes is desired.

Even further, an entanglement particle having magnetic properties is desired.

Therefore, there is a need for a fluid delivery system that is easily configurable to new delivery procedure and pre-treatment steps.

Further, there is a need for a disposable fluid delivery system that can be easily inserted and removed from a benchtop or portable device.

Yet further, there is a need for a fluid delivery system that is easily manufactured and customizable to suit varying fluid delivery needs.

SUMMARY OF THE INVENTION

The present invention relates to a sample preparation device. The sample preparation module is designed to identify and validate components for ultrasonic disruption and magnetic manipulation of nucleic acid molecules. In one embodiment, all processing steps occur within a disposable cartridge.

Automating the sample preparation process can greatly reduce the costs and increase the reproducibility of these techniques. In particular, automated gene sequencing systems require extensive processing of samples to prepare DNA for analysis. Most DNA sequencing approaches use an in vitro cloning step to amplify individual DNA molecules. Emulsion PCR isolates individual DNA molecules along with primer-coated beads in aqueous droplets within an oil phase. PCR then coats each bead with clonal copies of the DNA molecule followed by immobilization for later sequencing. Emulsion PCR is used in the methods by Marguilis et al. (commercialized by 454 Life Sciences), Shendure and Porreca et al. (also known as "polony sequencing") and SOLiD sequencing, (developed by Agencourt, now Applied Biosystems). Another method for in vitro clonal amplification is bridge PCR, where fragments are amplified upon primers attached to a solid surface. The single-molecule method developed by Stephen Quake's laboratory (later commercialized by Helicos) skips this amplification step, directly fixing DNA molecules to a surface.

Since both sonicated DNA fragments can contain single-stranded ends, most procedures include a step to end-repair the DNA prior to ligation into blunt-ended vectors (10,11). A combination of T4 DNA polymerase and Klenow DNA polymerase are used to "fill-in" the DNA fragments by catalyzing the incorporation of complementary nucleotides into resultant double-stranded fragments with a 5' overhang. Additionally, the single-stranded 3'-5' exonuclease activity of T4 DNA polymerase is used to degrade 3' overhangs. The reactions included the two enzymes, buffer, and deoxynucleotides and are incubated at about 37° C. The fragments are concentrated by ethanol precipitation followed by resuspension in kinase buffer, and phosphorylation using T4 polynucleotide kinase and rATP. The polynucleotide kinase is removed by phenol extraction and the DNA fragments are concentrated by ethanol precipitation, dried, resuspended in buffer, and ligated into blunt-ended cloning vectors. Since, a significant portion of sonicated DNA fragments are easily cloned without end-repair or kinase treatment, these two steps can be combined without significantly affecting the overall number of resulting transformed clones.

Currently, following fragment end-repair, the DNA samples are electrophoresed on a preparative low-melting temperature agarose gel versus a size marker, and after appropriate separation, the fragments in the size range from 1-2 Kbp and 2-4 Kbp are excised and eluted separately from the gel. Alternatively, the fragments can be purified by fractionation on a spin column such as a Sephacryl S-500.

The sample preparation process of the instant invention can prepare fragments of DNA and RNA in a size range of between 100 and 10,000 base pairs. The exact distribution of sizes can be varied by changing concentrations of surfactants, the surfactants used or the frequency of sonication. The ability to produce fragments in the desired size range obviates the need for electrophoresis or column isolation. This also increases the overall yield of useful fragments by eliminating the need for addition purification steps.

The sample preparation module allows for disruption of cells, sizing of DNA and RNA, concentration and cleaning of the material. Additional chambers in the cartridge can be used to deliver the reagents necessary for end-repair and kinase treatment. Enzymes can be stored dry and rehydrated in the cartridge or added to the cartridge just prior to use.

The present invention provides an apparatus and method for transmitting a plurality of fluids. A rotating valve comprising a rotating reservoir insert having a plurality of reservoirs is situated within a cartridge body. The rotating valve contains reservoirs for containing fluid; chambers for pre-treating fluid; a plurality of fluid paths for connecting the reservoirs and chambers to external ports; and pass-through channels for transmitting fluids.

The use of a rotating design allows for a single plunger to draw and push fluid samples without the need for a complex valve system to open and close at various times. This greatly reduces potential for leaks and failure of the device. Furthermore, the use of a plunger allows for greater configurability in adjusting the amount of fluid drawn.

The reservoir insert is injected molded allowing for varied configurations with minimal costs. The exterior of the reservoir insert is cylindrical to allow free rotation about its axis when encased in the cartridge body. The interior section of the reservoir insert can be modified to include any size or shape reservoir or pre-treatment chamber.

Customized rotating valves retain the same exterior shape and dimensions and can be inserted into existing equipment. The processing protocol of the instrument is easily modified to account for any new chambers, sample sizes, processing times, or port locations.

The rotating valve can be stored in position leaving all ports and vents closed allowing for long-term storage and shipping of the rotating valve with liquid and solid reagents loaded within the valve.

In one form, the invention comprises a sample preparation chamber for breaking apart a sample to obtain nucleic acid molecules. A shearing force is applied in the presence of a size stabilizer to both break apart the sample and obtain nucleic acid fragments in the desired size range.

The invention comprises, in one form thereof, a method for utilizing magnetic entanglement nanoparticle containing a target analyte binding element to bind the nucleation nanoparticle to a target analyte. The magnetic entanglement nanoparticle is capable of being manipulated within a magnetic field. As the magnetic entanglement nanoparticle is attached to the target analyte the target analyte is indirectly manipulated by the application of a magnetic field.

In one form, the target analyte binding element links directly to the particle surface. Optionally, the target analyte binding element is attached to the magnetic entanglement nanoparticle via intermediate connecting groups such as, but not limited to, linkers, scaffolds, stabilizers or steric stabilizers. The intermediate connecting group can be of variable size, architecture and chemical composition to interconnect the magnetic entanglement nanoparticle(s) and the target analyte binding element(s) into a multifunctional entity. In another embodiment the magnetic entanglement nanoparticle further contains a catalytic material. Magnetic entanglement nanoparticles are defined as capable of forming bonds to polymeric nucleic acids under certain conditions which can be released under certain other conditions.

In one embodiment, the magnetic entanglement nanoparticles are released from the nucleic acid molecule via the application of heat. Temperatures around 95° C. have been shown to effectively release the magnetic entanglement nanoparticles. In another embodiment the magnetic entanglement nanoparticles are released from the nucleic acid molecule via an elution solution. The elution solution may be a detergent or salt. In a preferred embodiment, the elution solution are phosphates or citrates. In on embodiment the elution solution is a potassium or sodium phosphate or citrate.

In one embodiment, the target analyte binding group functionalized particle require improved colloid stability to prevent agglomeration. Therefore, a colloid stabilizer, such as a hydrophilic chain or ionic group, is added or connected to a linking group that links to the particle. These groups assist in limiting the nanoparticles size during the particle generation stage.

It is an object of the invention to prepare nucleic acid samples within a desired size range.

One advantage of the invention, is a high yield of nucleic acid from the sample preparation.

Another advantage of the invention, is that it can be used with any nucleic acid sample source, including live tissue, bacterial cells, spores, insects, plants, and viral cells.

Yet another advantage of the invention, is that the nucleic acid produced is pure and clean, without contamination by other biological materials such as proteins, lipids, and cellular debris.

An even further advantage of the invention, is that the sample preparation process generates a high overall yield because most of the fragments are in a usable size range.

Another advantage of the present invention is that the utilization of magnetic entanglement nanoparticles allows for sample concentration by applying a magnetic field without additional processing steps.

A further advantage of the present invention is that the utilization of magnetic entanglement nanoparticles allows for rapid manipulation of target analytes thereby reducing diffusion and reaction times.

BRIEF DESCRIPTION OF THE DRAWINGS

The present invention is disclosed with reference to the accompanying drawings, wherein.

Corresponding reference characters indicate corresponding parts throughout the several views. The examples set out herein illustrate several embodiments of the invention but should not be construed as limiting the scope of the invention in any manner.

DETAILED DESCRIPTION

The automated sample preparation device of the instant invention provides an automated solution for preparing a biological sample for analysis. The device contains a rotating valve having a number of chambers to perform the various steps required to obtain a usable sample.

The rotating valve is a two piece construction capable of various positioning to allow the passage of fluid contained in the reservoirs into the fluid paths. The two piece design allows for easy manufacturing and assembly. The design further allows for the rotating valve to be a disposable piece in instruments requiring a plurality of fluids. In one embodiment, the rotating valve is a single use piece for use in detection devices. The rotating valve contains the necessary fluids for biological testing and further is capable of being injected with a field sample.

Figure 1A:
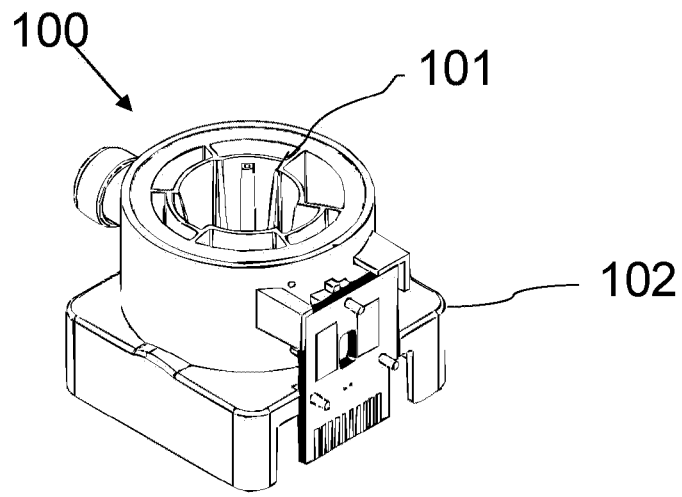
FIGS. 1A-1B show a graphical representation of a rotating valve according to one embodiment.
Figure 1B:
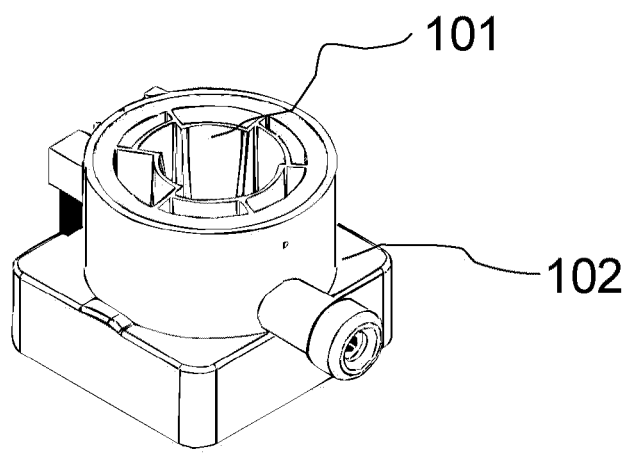

Referring to FIGS. 1A-1B there is shown an assembled rotating valve of the instant invention. The rotating valve comprises two main components. The reservoir insert 101 is contained within the cartridge body 102. The rotating valve 100 is a disposable component containing a plurality reservoirs capable of storing a plurality of fluids. In one embodiment, the reservoir insert 101 and the cartridge body 102 are both formed through injection molding techniques.

In one embodiment a chip containing biological probes is affixed to the cartridge body 102. The fluid contained in the reservoirs is transferred to contact the chip containing biological probes initiating reaction or detection chemistry. The chip is in communication with a detection device such as a bench-top or portable detection device to indicate the presence of target biological probes in any sample. The rotating valve 100 is inserted into a detection device that is in electrical communication with the chip. The detection device further affixes the cartridge body 102 into a fixed position.

Figure 2:
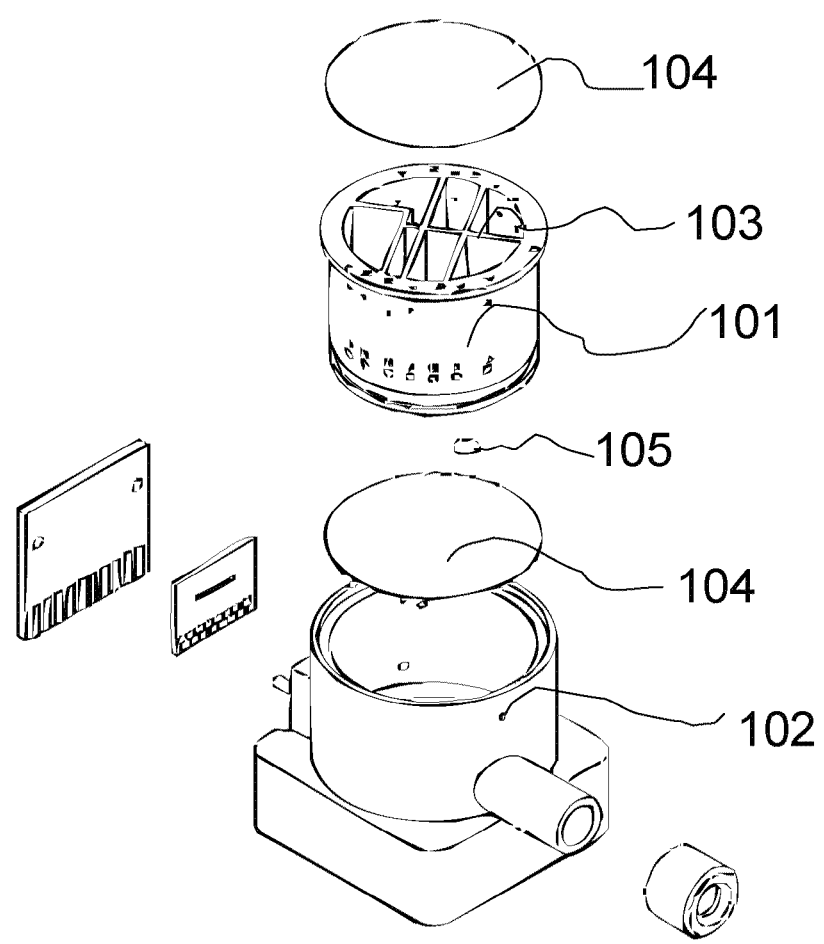
FIG. 2 shows an expanded view of a rotating valve according to one embodiment.

Referring to FIG. 2 there is shown an exploded view of the instant invention. The reservoir insert 101 is capable of containing a plurality of fluids in the various reservoirs 103. The heat seal films 104 seal the fluids into the reservoir insert and prevent leaks while allowing for the injection of samples. The heat seal films 104 seal the reservoirs from the outside environment. The heat seal films 104 further allow for fluid to be added to or removed from the reservoirs without compromising the integrity of the seal. In one embodiment, the heat seal films 104 improve energy transfer into and out of the reservoirs and chambers of the reservoir insert 101. Energy transfer includes but is not limited to heat, ultrasonic and magnetic. Optionally, a filter 105 is placed in-line with particular fluid paths to filter large solids from the fluid. In one embodiment Once the heat seal films 104 are sealed onto the reservoir insert 101 the reservoir insert 101 is affixed to the cartridge body 102. In one embodiment, the reservoir insert 101 "snaps into" the cartridge body 102. It is understood that the heat seal films 104 can be sealed to the reservoir insert 101 after the reservoir insert 101 is affixed to the cartridge body 102.

Figure 3A:
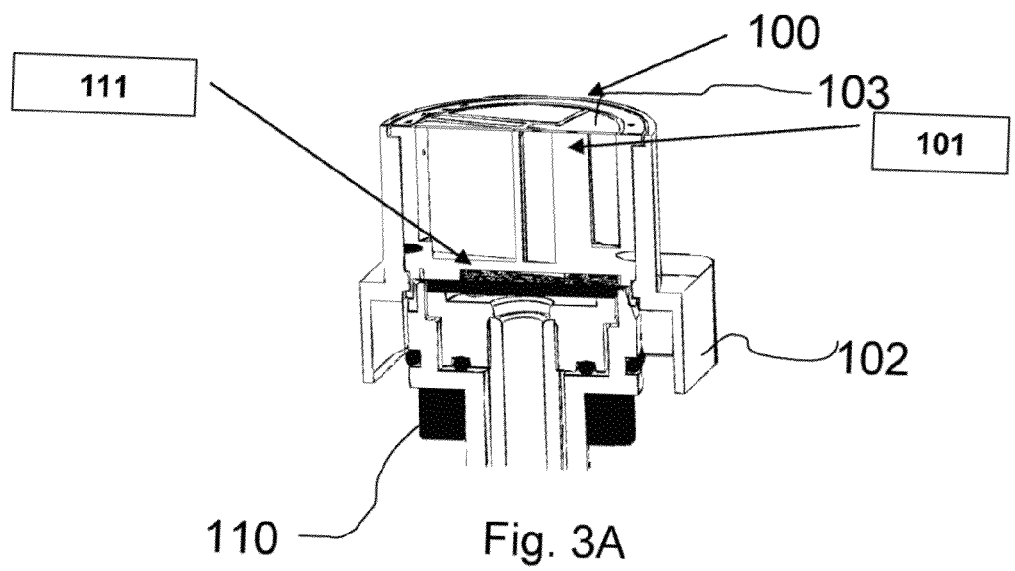
FIG. 3A shows a cross-sectional view of a rotating valve according to one embodiment.
Figure 3B:
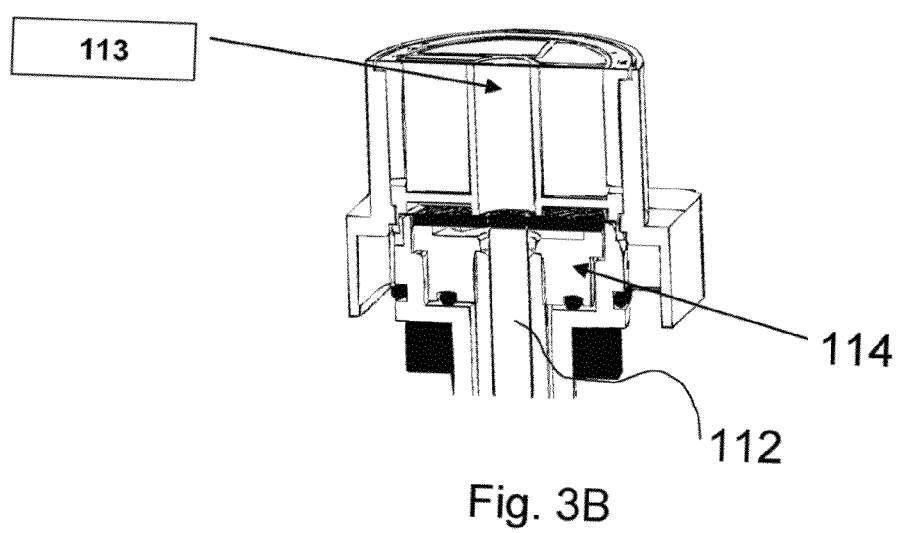
FIG. 3B shows a cross-sectional view of a rotating valve according to one embodiment having an electromagnet and sonicator built into the valve.
Figures 4A, 4B:
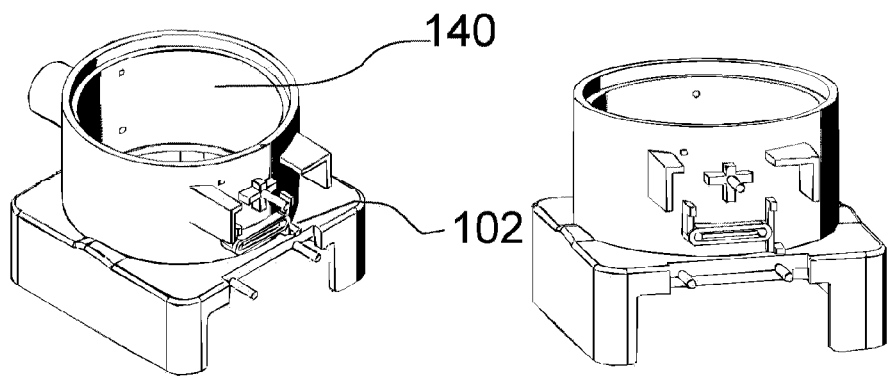
FIGS. 4A-4D show a graphical representation of the cartridge body according to one embodiment.
Figures 4C, 4D:
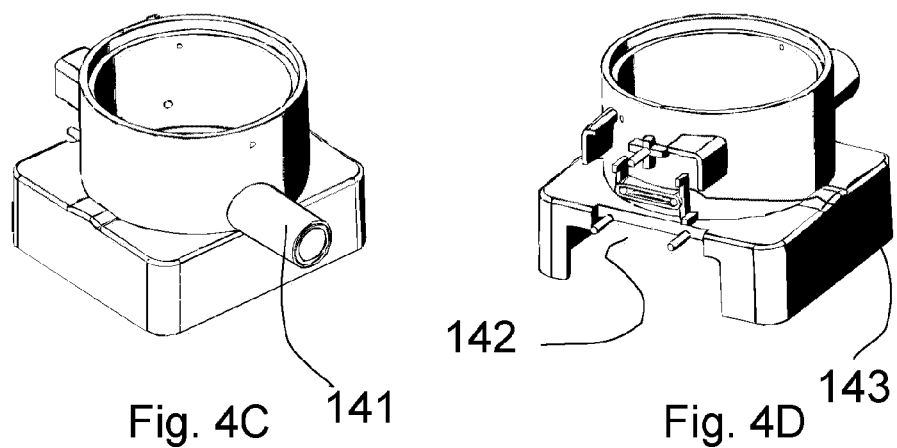

Referring now to FIGS. 3A-3B there is shown across sectional view of the rotating valve 100. The rotating valve 100 is set onto a drive mechanism 110. The drive mechanism 110 is capable of rotating the reservoir insert 101 to the desired configuration. The drive mechanism 110 rotates the reservoir insert 101 while the cartridge body 102 remains stationary. In one embodiment the drive mechanism has an optional heater 111. The heater is capable of heating the fluids contained in the reservoirs 103 to the desired temperature. Alternatively, heating chambers are strategically positioned above the heater to heat the fluid in the chamber without significantly heating the fluids in the reservoirs 103. In one embodiment, the heat film seals 104 facilitate this heating without significantly heating the fluids in the reservoirs 103. Treatment chambers are incorporated into the reservoir insert 101 to facilitate mixing, heating, disrupting, pressurization or any other treatment process.

In one embodiment the drive mechanism has a disruptor 112. The disruptor is capable of mixing or breaking down the fluids contained in the reservoirs 103 by applying an ultrasonic force. Alternatively, the rotating valve has a disrupting chamber 113 for mixing fluids in a chamber distinct from the reservoirs. In one embodiment small beads are located in the disrupting chamber or reservoir to assist in mixing fluids or breaking down samples. The disrupter 112 applies an ultrasonic force causing the beads to become excited and move through the fluid. In one embodiment a magnet 114 is utilized to generate an electric field. The magnet can pull or push magnetic particles in the reservoir insert. The magnet 114 can concentrate a sample of magnetic particles or speed up the diffusion process by guiding any magnetic particles.

A mechanical force, such as a shearing force, is applied to a biological sample to break down the sample to release nucleic acid molecules. A size stabilizer is present to obtain nucleic acid molecules within a usable size range. In one embodiment, the sample material is shredded with high speed nano-particles utilizing sonication. This process breaks down cells, tissue or other materials to release nucleic acid molecules. It is understood that the mechanical force can be any force suitable for tearing apart the sample to release the nucleic acid molecules. Suitable mechanical forces include, but are not limited to sonication, nebulization or homogenization. In one embodiment, the nucleic acid molecules are reduced to sizes between 200 and 10,000 base pairs in length. In another embodiment the nucleic acid molecules are reduced to sizes between 300 and 3,000 base pair in length. In another embodiment the nucleic acid molecules are reduced to sizes between 400 and 2,000 base pair in length. In another embodiment the nucleic acid molecules are reduced to sizes between 200 and 500 base pair in length. It is understood that the desired base pair length will vary depending on the downstream sample processing technique. Sample processing techniques include, but are not limited to hybridization, PCR, real-time PCR, reverse transcription-PCR, "lab-on-a-chip" platforms and DNA sequencing.

Biological samples include all biological organisms which contain nucleic acids. Including but not limited to bacteria, spores, blood, tissues, fungi, plants and insects.

Figure 26:
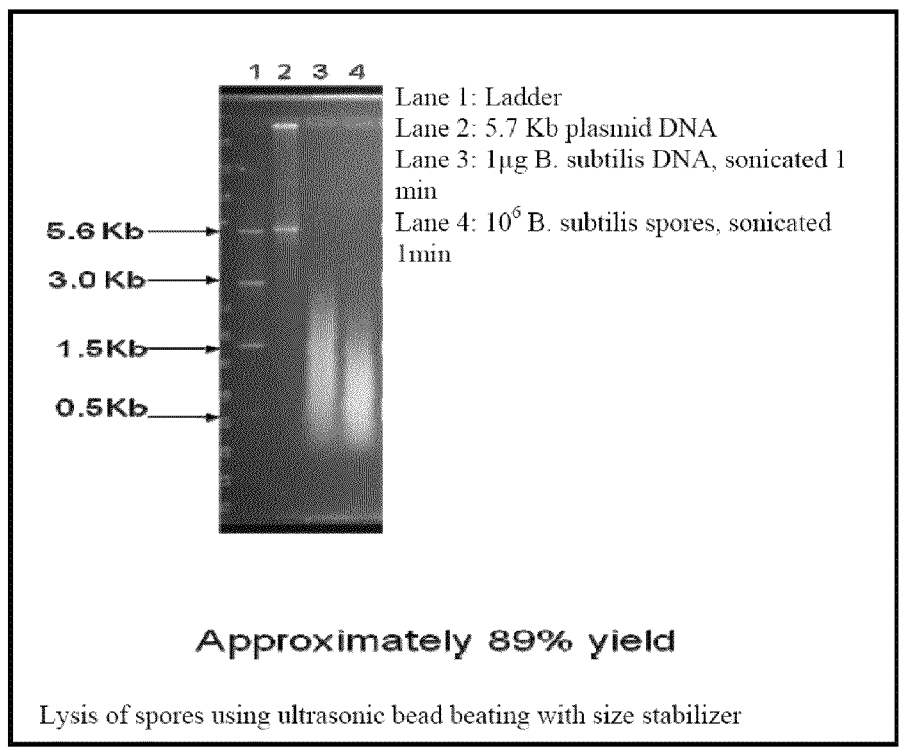
FIG. 26 demonstrates the effective release of nucleic acid molecules from the lysis of spores using ultrasonic bead beating with size stabilizer.

Bead beating is a process to isolate nucleic acid molecules from samples. It is a robust approach which is well suited for use with spores or tissue samples. In bead beating, glass beads of about 100 microns in diameter are used to crush the sample to release the nucleic acid molecules. The particles are moved using an ultrasonic source. FIG. 26 demonstrates the effective release of nucleic acid molecules from spore samples.

Sample Disruption

In one embodiment, disrupting beads such as glass beads of about 100 microns in diameter are used to break apart a sample and release nucleic acid molecules. The beads are vibrated using an ultrasonic source to generate a shearing force on the sample. In one embodiment, for sample suspensions from about 0.1 ml to 0.5 ml of water, containing from about 0.1% to 1% nucleic acid, an ultrasonic power level of about 3 to 7 watts is used for a period of from about 1 to 3 minutes. The volume of glass beads used in the sample is preferably between about 10% to 50% of the volume of the total suspension. The ultrasonic frequency used to agitate the glass beads is conveniently 20 KHz, from a commercial device such as the Branson Sonifier 150. It is understood that frequencies from about 10 KHz to 100 KHz could be suitable depending on the sample parameters.

In another embodiment, the shearing force is applied by a nebulizer or a homogenizer.

The addition of size stabilizers in the sample preparation of this invention results in a high yield of nucleic acids of limited size range. The size stabilizers of this invention include detergents, surfactants and soaps. Preferred stabilizers include anionic surfactants, and most preferred stabilizers include sodium dodecylsulfate, and sodium dodecylbenzenesulfonate. The size stabilizer is present in the sonicated suspension in an amount between about 0.1% and 10%, and more preferably, in an amount between about 0.2% and 2% and most preferably, in an amount between about 0.5 and 1.5%.

Other size stabilizers of this invention include chaotropic salts such as guanadium thiocyanate. Such salts are known to disrupt the normal folding of proteins associated with nucleic acids, thereby releasing the nucleic acids in free form.

Figure 27:
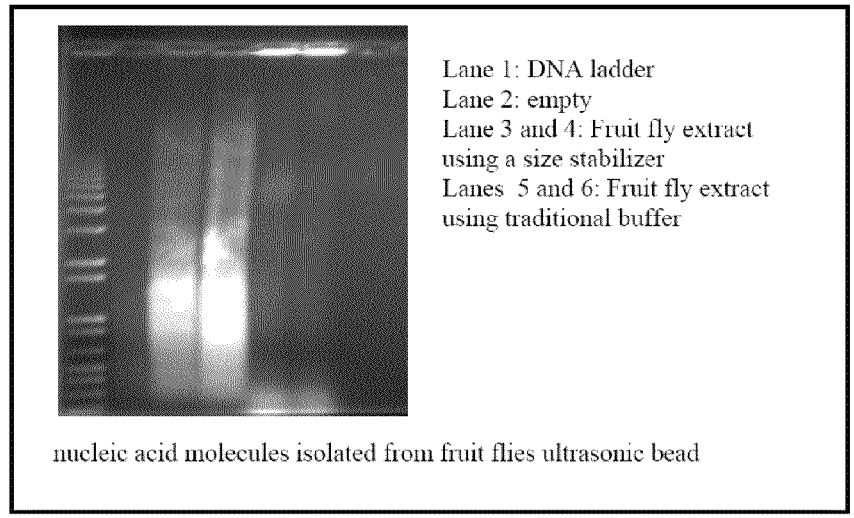
FIG. 27 demonstrates nucleic acid molecules isolated from fruit flies and that the addition of a size stabilizer in lanes 2 and 3 protect the nucleic acid molecules from over shearing, whereas the samples without the denaturants were sheared to a level well below 100 base pairs.
Figure 28:
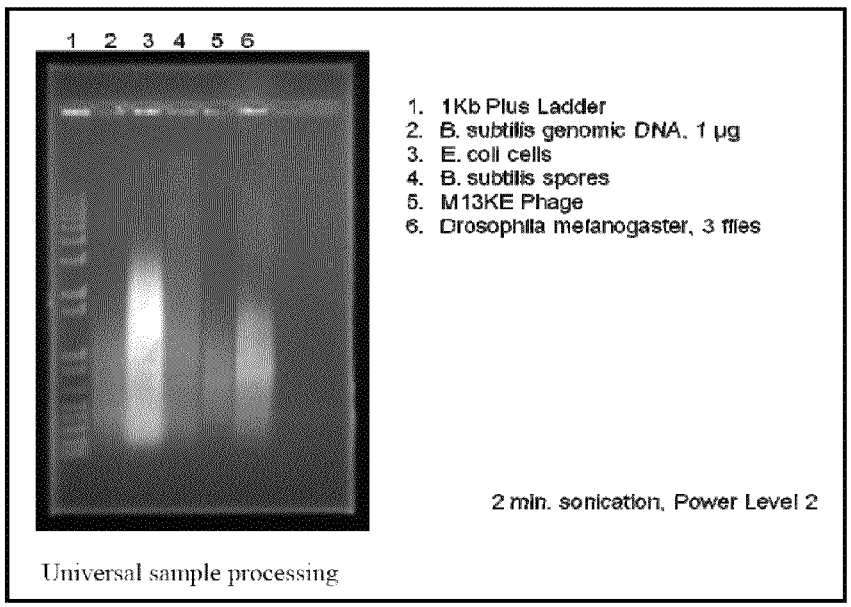
FIG. 28 shows that using this process the nucleic acid molecules from a wide variety of different samples can be treated with the same power levels and time of sonication to give the same size distribution of fragments.

Without a size stabilizer present, the nucleic acid molecules tend to degrade during the lysis step. The ultrasonic bead beating shears the nucleic acid molecules into short fragments that are less than 100 bases long (See FIG. 27, lanes 5 and 6). For most applications, fragments need to be larger than 100 bases. In one embodiment, the preferred range is between 400 to 2000 bases. As shown in FIG. 28, a series of tests were performed to sonicate purified DNA and RNA sheared polymers to no smaller than 400 bases. In complex samples, nucleic acid molecules stick to membranes and proteins while continuing to break down to smaller fragments. To overcome this problem, the lysis buffer is modified to contain a size stabilizer such as a detergent like sodium dodecyl sulfate (SDS). In another embodiment, the size stabilizer is guanadinium hydrochloride or potassium bromide. As shown in FIG. 27, the addition of the size stabilizer shown in lanes 3 and 4 protects the nucleic acid molecules from over shearing. The samples without the size stabilizer were sheared to well below 100 bases, as shown in lanes 5 and 6.

FIG. 26 demonstrates the effective release of nucleic acid molecules from spore samples. To determine efficiency of spore lysis, the maximum amount of nucleic acid output expected from the spores was estimated and compared to the amount measured on the gel in FIG. 26. Utilizing this technique, the method provided an estimate of 85-90% efficiency. Alternatively, spore lysis efficiency can be measured by determining spore survival after sonication. As shown in Table 1, based upon survival assays, the efficiency after two minutes of sonication during experiments was 86% of spores were opened.

TABLE 1

Efficiency of spore lysis as determined by spore survival (Spore Basis)

| Sonication time | # spores survived | % efficiency |
|---|---|---|
| No sonication | 235 | |
| 30 sec. | 105 | 55% |
| 1 min. | 61 | 74% |
| 2 min. | 32 | 86% |

Bead beating with sonication however, has had a drawback in that the nucleic acid molecules are degraded during the lysis step. The ultrasonic bead beating shears the nucleic acid molecules to short fragments that are no longer usable. For most uses, fragments need to be larger than 100 bases long. Bead beating often results in fragments much less than 100 bases long.

By utilizing a size stabilizer in solution with the sample the nucleic acid molecules can be protected to limit the minimum size achievable to more desirable base pair length. The addition of size stabilizers in the sample preparation results in a high yield of nucleic acids of limited size range. The size stabilizers include detergents, surfactants, polymers, salts and soaps.

Other size stabilizers of this invention include chaotropic salts such as guanadium thiocyanate. Such salts are known to disrupt the normal folding of proteins associated with nucleic acids, thereby releasing the nucleic acids in free form.

Suspension of the biological sample is done by mixing with a buffer. To retain the desired sample size the buffer serves as a size stabilizer. The size stabilizer is a water solution which may contain salts, detergents, co-solvents or polymers. The size stabilizer prevents the subsequent shearing step from producing fragments of nucleic acid molecules that are too small to be useful in operations such as hybridization, sequencing and polymerase chain reaction (PCR) amplification. For hybridization, fragments of nucleic acid molecules that are smaller than about 18 base pairs lose specificity and are unstable at ambient temperatures. For genetic sequencing and PCR applications, nucleic acid molecule fragments from about 200 to about 500 base pairs are desirable. Use of a pure water buffer gives nucleic acid molecule fragments less than about 100 base pairs, which are too small for many applications.

Use of the size stabilizer allows the gathering of nucleic acid molecule fragments in a desired base pair range. In traditional bead beating processes the mechanical shearing force is turned off after a particular time to maximize the amount of nucleic acid molecule fragments in the desired base pair range. However, because the process is time sensitive a large range of base pair lengths remain present in the sample. By utilizing a size stabilizer the base pair length of most of the sample can be fragmented to the desired base pair range. In one embodiment, at least 60% of the nucleic acid molecule fragments are within 50% of the length of the median nucleic acid molecule fragment base pair length in the sample. Said another way, if the median nucleic acid molecule fragment has 400 base pairs, 60% of the sample would have between 200 and 600 base pairs. In another embodiment, at least 75% of the nucleic acid molecule fragments are within 50% of the length of the median nucleic acid molecule fragment base pair length in the sample. In yet another embodiment, at least 75% of the nucleic acid molecule fragments are within 30% of the length of the median nucleic acid molecule fragment base pair length in the sample.

Figure 35:
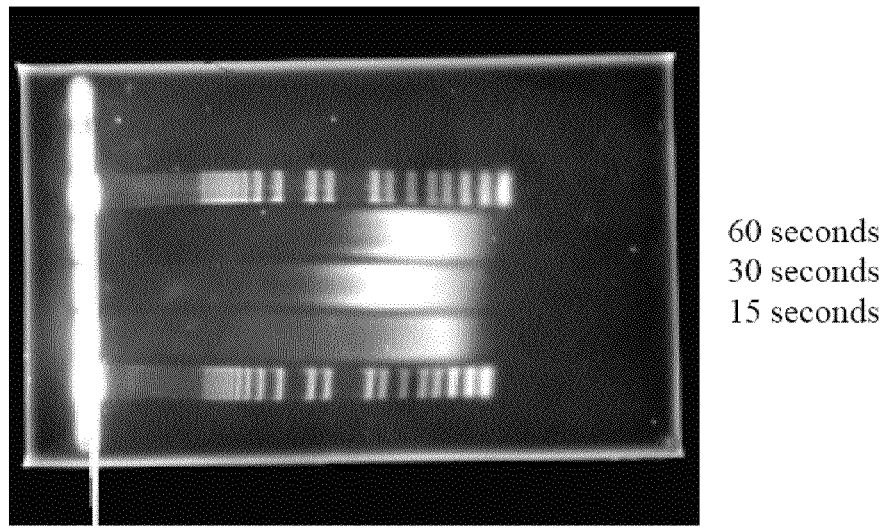
FIG. 35 demonstrates the recovery of nucleic acid molecules from e-coli and that longer sonication times do not change the size distribution.

Without a size stabilizer present, the nucleic acid molecules tend to degrade when applying a mechanical force such as sonication. The ultrasonic bead beating with a size stabilizer present shears the nucleic acid molecules into short fragments that are less than 100 bases long (See FIG. 27, lanes 5 and 6). For most applications, fragments need to be larger than 100 bases. As shown in FIG. 35, a series of tests were performed to sonicate purified DNA and RNA sheared polymers to no smaller than 400 bases, even under lengthy sonication times. In complex samples, nucleic acid molecules stick to membranes and proteins while continuing to break down to smaller fragments. To overcome this problem, the lysis buffer is modified to contain a size stabilizer such as a detergent like sodium dodecyl sulfate (SDS). As shown in FIG. 27, the addition of the size stabilizer shown in lanes 3 and 4 protects the nucleic acid molecules from over shearing. The samples without the size stabilizer were sheared to well below 100 bases, as shown in lanes 5 and 6.

The size stabilizer is contained in a protective buffer solution. It is understood that the protective buffer may contain numerous size stabilizers to achieve the desired base pair range. Salts which may be used in the protective buffer include, sodium phosphate, guanidinium hydrochloride and dextran sulfate. The protective buffer may further contain detergents such as sodium dodecyl sulfate, sodium dodceyl benzene sulfate, and polyethyleneglycol. Many commercial anionic surfactants such as Alkanol XC may also be used. In another embodiment the protective buffer includes co-solvents. Co-solvents include dipole aprotic solvents such as dimethylsulfoxide, dimethyl formamide, dimethylacetamide, hexamethyl phosphoramide and tetramethylurea. In another embodiment the protective solution contains polymers such as poly vinyl alcohol, polyethylenimine, poly acrylic acid and other polymeric acids. The concentration of the salts, detergents, co-solvents and polymers may range from 10 mM to 5M, and is preferably between about 100 mM to about 1M.

For mechanical shearing such as bead disruption to be used as a universal sample preparation approach, it is necessary to characterize and optimize operating parameters with respect to different target material (DNA, RNA or protein) and their source (environmental, blood, or tissue). Although a single system is suitable for disruption different sample types, to optimize results parameters such as power input and the duration of applying sonic agitation may vary with respect to different cell types. Furthermore, it is understood that the concentration of the size stabilizer, the size of the glass beads and the inclusion of enzymes such as collagenase and hyaluronase are all further embodiments of the invention and are no way limiting.

It is understood that magnetic particles, glass beads or a combination of both can be used for disruption without departing from the invention. In one embodiment the magnetic particles are formed of iron oxides. In one embodiment the particles are in the 40-200 nm size range. The particles can be accelerated using an ultrasonic force and can shred the sample. In one embodiment, glass beads are used in the extraction mixture for efficient lysis of spores.

In one embodiment the mechanical force used to release the nucleic acid molecules is sonic vibration accomplished by contacting a container of the fragments suspended in protective buffer with source of sonic vibrations. Such a source may be a commercial ultrasonic transducer or a piezo electric crystal activated by an AC voltage. Such devices are well known to those skilled in the art. Shearing frequencies can be from 10,000 Hz to 10 MHz, preferably between 20 KHz and 4 MHz, and most preferably between 20 KHz and 40 KHz. To assist the shearing of protected nucleic acid molecules samples such as, for example, spores, small beads may be added to the sample. The sonic induced movement of the beads breaks the spore walls to release the nucleic acid molecules contained within. The beads may range in size from about 1 micron to about 1 mm, preferably from about 10 microns to about 500 microns and most preferably from about 50 microns to about 200 microns. The beads may be a metal such as stainless steel, glass or a dense metallic oxide such as zirconium oxide. The time required for shearing the nucleic acid molecules depends partly on the size of the sample and power transmitted from the transducer to the sample. However, when the sheared sample reaches a steady state, which depends on the composition of the protective buffer, there is no further change in the nucleic acid molecules size distribution with further sonication. In practice, sonication times of 15 seconds to 2 minutes at a power level of 1 to 2 watts with a sample size of 100 ul of buffer containing 1 microgram of nucleic acid molecules are sufficient to reach a steady state.

In another embodiment, the sample preparation process further includes the addition of RNase inhibitors to prevent sample degradation. In one embodiment, the sample preparation process includes diethylpyrocarbonate (DEPC), ethylene diamine tetraacetic acid (EDTA), proteinase K, or a combination thereof.

In another embodiment, the presence of a size stabilizer also stabilizes RNA. The SDS and guandinium thiocyanate disrupt the RNAses in the sample thus preserving the RNA.

In one embodiment the magnetic nanoparticle is a magnetite nanoparticle. Magnetite particles are common in nature, and can be collected from beach sands at the edge of the ocean by screening with a magnet. Grinding these particles will produce a relatively coarse magnetic powder. Smaller sized particles can be produced by adding a solution of mixed ferric and ferrous chloride to a stirred aqueous alkaline solution of sodium or ammonium hydroxide. Even smaller sized particles are produced by thermal decomposition of iron acetonylacetonate in dibenzyl ether in the presence of hexadecanediol, oleyl amine and oleic acid. Numerous methods for making magnetite are known. For example, Sun et al. discloses slowly adding a mixture of ferric and ferrous chloride into stirred ammonia. *Langmuir*, 2009, 25 (10), pp 5969-5973. U.S. Pat. No. 4,698,302 teaches mixing ferrous and ferric chloride with sodium hydroxide. Samanta et al, discloses adding ammonia to a stirred mixture of ferric and ferrous chloride in an inert atmosphere. Journal of Materials Chemistry, 2008, 18, 1204-1208. Duan et al. teaches dissolving iron oxide in oleic acid to form a complex that forms magnetite nanoparticles when heated to 300 degrees C. *J. Phys.* nucleic acid molecule *Chem. C*, 2008, 112 (22), pp 8127-8131. Additionally, Yin et al. discloses thermally decomposing iron pentacarbonyl in the presence of oleic acid, Journal of Materials Research, 2004, 19, 1208-1215.

Sample Types Processed

Numerous types of samples can be proceed by applying a shear force to break apart the sample to release nucleic acid molecule. The sample preparation process is suitable for use on liquids, solids, soil samples, animal tissue, insect carcasses, DNA, bacterial cells, spores and viruses. As shown in FIG. 28, several disparate samples were processed using identical parameters. Samples of purified DNA, bacterial cells, spores, viruses and fruit flies were all treated using the following technique: each sample was subjected to sonication treatment for two minutes in the presence of magnetic nanoparticles and 100 micron glass beads. As shown in FIG. 28, all sample types provided a similar fragment distribution.

As a variety of types of samples can be used, a single system can be used with a wide variety of target organisms without the need to modify the preparation process. Furthermore, even if a sample contains two different targets, nucleic acid molecules can be purified from both components. For example, standard procedures may not work with a sample containing both a virus and a spore—either the parameters must be set to efficiently lyse the spores, in which case viral material is lost, or set to maximize the viral sample, in which case the spores are not lysed. Thus the benefits of the inclusion of a size stabilizer or evident.

By utilizing a single sample preparation technique the potential for false negatives is reduced. As the size stabilizer limits the range of base pair lengths for the nucleic acid molecules, the potential for material loss do to over-sonication is decreased.

In one embodiment, the sample preparation system works with small quantities and produces a narrow distribution of nucleic acid molecule fragments. Optionally, the preparation system passes sample through steps that filter the sample prior to applying a shear force.

In one embodiment, the nucleic acid molecules are used for PCR application after preparation. It is known that PCR applications do not work successfully in the presence of detergents and alcohol. Therefore, for PCR application and additional filtering or cleaning step is utilized to prepare the sample prior to testing.

FIG. 28, demonstrates that using this process the nucleic acid molecules from a wide variety of different samples can be treated with the same power levels and time of sonication to give the same size distribution of fragments.

In one embodiment, the process further contains the steps necessary to clean the nucleic acid molecules. After release of the nucleic acid molecules and shearing to a useful size range, it is advantageous to clean the nucleic acid molecules from cell debris, proteins, sonication beads and the protection buffer to provide a purified nucleic acid molecule solution in a buffer compatible with subsequent nucleic acid molecule operations and procedures.

In one embodiment, a magnet is utilized to generate an magnetic field. The magnet can pull or push magnetic particles. The magnet can concentrate a sample of magnetic particles or speed up the diffusion process by guiding any magnetic particles.

In one embodiment, magnetic nanoparticles are located in a sample chamber along with a target analyte. The magnetic nanoparticles have an affinity for the target analyte. By attaching the magnetic nanoparticles to the target analyte and applying a magnetic field the target analyte is manipulated to desired locations within the sample chamber.

In one embodiment, a precipitation buffer in solution with the target analyte fragments and the magnetic nanoparticle. The precipitation buffer precipitates the target analyte out of solution and the target analyte is drawn to the magnetic nanoparticles. The precipitation buffer can be any buffer that precipitates the target analyte from the solution. For proteins, the precipitation buffer includes, but is not limited to organic precipitants such as, ammonium sulfate, trichloroacetic acid, acetone, or a mixture of chloroform and methanol. For nucleic acid molecules such as DNA suitable precipitation buffers include, but are not limited to, water miscible organic solvents, acetone, dioxane and tetrahydrofuran. While examples of precipitation buffers are provided, it is understood that any suitable precipitation buffer can be utilized without deflecting from this claimed invention.

In another embodiment, the magnetic nanoparticles contain superparamagnetic particles. The superparamagnetic particles include metal oxides, such as iron oxides. A preferred iron oxide is magnetite ($Fe_3O_4$).

Once the sample is lysed, the nucleic acid molecules can be magnetically separated from the reminder of the sample. The nucleic acid molecules bind to magnetic particles. In one embodiment, the binding occurs in a high salt/alcohol condition and is eluted using a low salt chelating buffer such as sodium citrate with increased temperature. In one embodiment the sample is heated to at least 60° C. to increase the yield from elution.

Once the magnetic nanoparticles are attached to the target analyte a magnetic field is applied to the reaction chamber. The application of the magnetic field causes the magnetic nanoparticles and any attached target analytes to concentrate in one portion of the reaction chamber. The sample is pulled from the concentrated region of the sample chamber providing a large amount of target analytes comparative the amount of volume extracted. By concentrating the sample more sensitive tests can be preformed.

In another embodiment, the magnetic field holds the magnetic nanoparticle steady as the remaining sample is removed from the chamber. The binding force between the magnetic nanoparticle and the target analyte is sufficient to prevent the target analyte from being removed.

In one embodiment a dispersion of magnetic nanoparticles is added to the sample. The mixture is then incubated at about 60° C. to facilitate the binding. A precipitation buffer is then added to the mixture. The bound complex of nucleic acid molecules and magnetite is then collected in a magnetic field. In one embodiment, the complex is collected on a side wall of the container so any unbound solids can fall to the bottom of the container for easy removal. The buffer and any unbound solids are then removed from the sample.

Optionally, additional rinse steps are used to purify the sample. The cleaning removes compounds which could inhibit binding of nucleic acid molecules. Suitable rinse solutions include, but are not limited to alcohol solutions such as ethanol. The complex can be washed with additional precipitation buffer, or a washing buffer that does not disturb the complex. After washing, the buffer is drained from the complex resulting in a purified, concentrated sample.

Suitable binding buffers are optionally added to the solution. Binding buffers for the nucleic acid molecule/magnetite complex are, for the most part, buffers in which nucleic acid molecules are insoluble. Precipitation of the nucleic acid molecules promotes binding of the nucleic acid molecules to the magnetite particles. The binding buffer for nucleic acid molecules and magnetite nanoparticles may contain water, sodium acetate, sodium chloride, lithium chloride, ammonium acetate, magnesium chloride, ethanol, propanol, butanol, glycogen or other sugars, polyacrylamide or mixtures thereof. In one embodiment the binding buffer is isopropanol. Binding of the nucleic acid molecules to the magnetite nanoparticles is not instantaneous. In one embodiment the mixture is incubated above room temperature to speed the binding process.

For further processing of the nucleic acid molecules, for some processes, it is necessary to remove the magnetite particles. In one embodiment the nucleic acid molecule is eluted from the complex of nucleic acid molecules and magnetite by heating a mixture of an elution buffer and the complex to 95° C. The magnetite can be collected by a magnetic field, or by centrifugation, providing purified nucleic acid molecules in elution buffer. In one embodiment the elution buffers contain a salt which interacts strongly with iron oxide surfaces. Preferred buffers are phosphate and citrate salt solutions.

Magnetic Manipulation:

In one embodiment, a magnet 114 is utilized to generate an electric field. The magnet can pull or push magnetic particles in the reservoir insert. The magnet 114 can concentrate a sample of magnetic particles or speed up the diffusion process by guiding any magnetic particles.

Magnetic entanglement nanoparticles are located in a sample chamber along with a target analyte. The magnetic entanglement nanoparticles have an affinity for the target analyte. By attaching the magnetic entanglement nanoparticles to the target analyte and applying a magnetic field the target analyte is manipulated to desired locations within the sample chamber.

In one embodiment, the target analyte binding element is attached to the magnetic entanglement nanoparticle via at least one intermediate connecting group such as, but not limited to linkers, scaffolds, stabilizers or steric stabilizers.

The nucleation nanoparticle contains particles that exhibit magnet properties. There are a number of particles that exhibit magnetic properties. In one embodiment cobalt, nickel, iron or a combination thereof is used to create a magnetic entanglement nanoparticle. Optionally, the magnetic entanglement nanoparticle further contains a catalytic particle. In one embodiment the catalytic particle is palladium, platinum, silver or gold.

In another embodiment, the entanglement nanoparticles contain superparamagnetic particles. The superparamagnetic particles include metal oxides, such as iron oxides. A preferred iron oxide is magnetite ($Fe_3O_4$).

In one form, a nickel-palladium nanoparticle, stabilized by a surface layer of 4-dimethylaminopyridine as described in Flanagan et al, Langmuir, 2007, 23, 12508-12520, is treated by adsorption with a plurality of ethidium bromide intercalator molecules to create nucleic acid binding sites. The ethidium moiety bonds to the nucleic acid polymer thereby attaching the nickel-palladium nanoparticle to the nucleic acid polymer.

In another form, a simple straight-chain scaffold molecule, such as oligoethylene glycol (PEG), is affixed with a nucleic acid binding element at one end and a linker at the other end. The nucleic acid binding element binds to the nucleic acid polymer and the linker binds to the magnet nucleation nanoparticle. The nucleic acid binding element is an intercalator, such as ethidium bromide, or a minor groove binder such as distamycin. The linker is a phenanthroline derivative. Hainfeld, J. Structural Biology, 127, 177-184 (1999) reports the advantage of phenanthroline derivatives in creating palladium particles. The scaffold may be a simple difunctional straight chain as shown, or may be a multifunctional branched scaffold connecting multiple catalytic nucleation nanoparticles or nucleic acid binding elements. The nucleic acid binding element bonds to the nucleic acid polymer, thereby attaching the nanoparticle to the nucleic acid polymer. It is understood that additional nucleic acid binding elements and intermediate connecting groups are within the scope and may be used.

Concentration of Target Analyte:

The sample containing the target analyte is located in a reaction chamber. The reaction chamber contains both the sample and magnetic entanglement nanoparticles. The magnetic entanglement nanoparticles bind to the target analyte. In one embodiment the reaction chamber further contains disrupting beads to assist in breaking apart samples to provide access to the target analyte.

Once the sample is lysed, the nucleic acid molecules can be magnetically separated from the reminder of the sample. The nucleic acid molecules bind to magnetic particles. In one embodiment, the binding occurs in a high salt/alcohol condition and is eluted using a low salt chelating buffer such as sodium citrate with increased temperature.

In one embodiment the sample is heated to at least 95° C. to increase the yield from elution.

Once the magnetic entanglement nanoparticles are attached to the target analyte a magnetic field is applied to the reaction chamber. The application of the magnetic field causes the magnetic entanglement nanoparticles and any attached target analytes to concentrate in one portion of the reaction chamber. The sample is pulled from the concentrated region of the sample chamber providing a large amount of target analytes comparative the amount of volume extracted. By concentrating the sample more sensitive tests can be preformed.

In another embodiment, the magnetic field holds the magnetic entanglement nanoparticle steady as the remaining sample is removed from the chamber. The binding force between the magnetic entanglement nanoparticle and the target analyte is sufficient to prevent the target analyte from being removed. Optionally, additional rinse steps are used to purify the sample.

Rapid Movement and Increased Sensitivity:

Typically in solution a target analyte is limited in movement by fluid flow and diffusion rates. To speed the movement of a target analyte through the system a magnetic field is applied to progress the magnetic entanglement nanoparticle to the desired location. The application of the magnetic field allows for rapid transport of the target anaylte from one chamber to another.

An array of sensors are used to rapidly detect the target analyte. A magnetic field is applied to guide the magnetic nanoparticles and attached analytes to the vicinity of a first sensor. A distinct magnetic field then guides the magnetic nanoparticles and any attached target analytes to a second sensor. The magnetic field is manipulated to move the target analytes to each sensor in the array. In one embodiment, the sensor binds a particular target analyte with enough force to prevent the magnetic field from breaking the bond. By systematically applying magnetic fields the analysis time is greatly reduced compared to normal diffusion analysis.

Magnetic Entanglement Nanoparticles:

Use of sols or clusters in the form of magnetic entanglement nanoparticles allows for the attachment of magnetic material to a target nucleic acid polymer or other target analyte. By applying a magnetic field to the sample the nucleic acid polymer can be manipulated via the attached paramagnet material.

The paramagnet nucleation nanoparticles are formed in solution with a stabilizer. In one embodiment a metal salt is used. A reducing agent, such as dimethylamineborane or sodium borohydride, is added to the solution. If needed, solvents and excess salts can be removed by centrifugation, decantation, washing, and resuspension of the metal clusters. Alternatively, a magnetic field can be applied to the solution holding the magnetic entanglement nanoparticles in place as a drain and rinse is applied.

Target Analyte Binding Element:

The target analyte binding element attaches to the magnetic entanglement nanoparticle, either directly or by way of an intermediate connecting group. The target analyte binding element further binds to the nucleic acid polymer. In one embodiment the target analyte binding element is a nucleic acid binding element such as a molecule, fragment or functional group that binds to nucleic acid polymers. Potential nucleic acid binding elements consist of intercalators, minor groove binders, cations, amine reactive groups such as aldehydes and alkylating agents, proteins, and association with hydrophobic groups of surfactants. In addition, functional groups such as aldehydes are used to create a connection by reaction with free amines in the nucleic acid. Other amine reactive groups such as Michael addition are suitable.

Examples of structures that form the basis for intercalating and minor groove binder structures are:

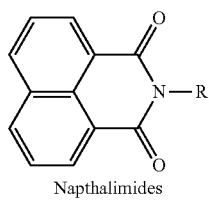
Napthalimides

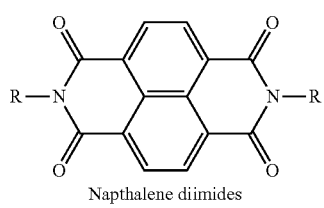
Napthalene diimides

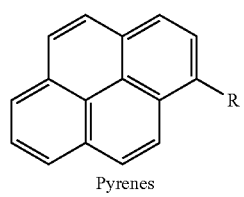
Pyrenes

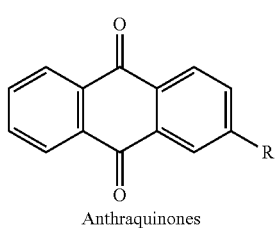
Anthraquinones

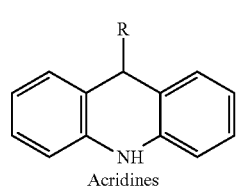
Acridines

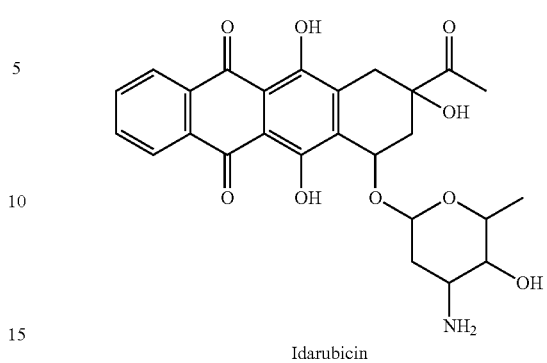
Idarubicin

The range of specific intercalator and minor groove binder structures is enormous as the field has been the subject of intense study for over 50 years. See R. Martinez and L Chacon-Garcia, Current Medicinal Chemistry, 2005, 12, 127-151. Therefore, the R groups include a broad range of organic functional groups. In many cases, interaction can be enhanced if R contains hydrogen bonding, cationic or hydrophilic character.

In addition, compounds such as cationic polymers, such as polyethyleneimine, interact with nucleic acid and have been proposed as gene carriers as evidenced by Xu et al, International Journal of Nanoscience, 2006, 5, 753-756 and Petersen et al, Bioconjugate Chemistry, 2002, 13, 845-854. Proteins are another well known class of materials that offer useful nucleic acid interaction and could be the basis for attaching nanoparticles to nucleic acids. Direct reaction with functional groups on the nucleic acid is also within the scope of this invention. For example, amine groups can be reacted with aldehydes to create a bond (Braun et al, Nano Letters, 2004, 4, 323-326)

In one embodiment the nucleic acid binding elements are specific binding agents that specifically target double-stranded nucleic acid molecules while not binding with single-stranded nucleic acid molecules. For example, minor-groove binding compounds specifically bind hybridized double-stranded DNA molecules, but do not bind to single-stranded oligonucleotide capture probes. In contrast, palladium chloride reagent indiscriminately binds to both the target molecules and capture probes. The binding element binds specifically to the target nucleic acid molecule while having little or no affinity towards non-target molecules. It is understood that the specific binding elements can include but are not limited to intercalators, minor-groove binding compounds, major-groove binding compounds, antibodies, and DNA binding proteins. The specific binding element binds to a specific site on a target nucleic acid without binding to non-desired areas. In one embodiment, the specific binding element is ethidium bromide. In alternative embodiments, the specific binding element is distamycin, idarubicin, or Hoescht dye.

In one embodiment the nucleic acid binding element also serves as a stabilizer as described below.

Stabilizers:

The magnetic entanglement nanoparticles are surface functionalized with stabilizers to impart desirable properties. These stabilized nucleation nanoparticles demonstrate colloid stability and minimal non-specific binding. Furthermore, the presence of the stabilizer in solution while forming the magnetic entanglement nanoparticle controls the nanoparticle size.

The stabilizer provides colloid stability and prevents coagulation and settling of the magnetic entanglement nanoparticle. The stabilizer further serves to limit the size of the magnetic entanglement nanoparticle during the formation process. In one embodiment, metal magnetic entanglement nanoparticle are formed in a solution containing stabilizer and metal ions. In one embodiment the stabilizers are chelating compounds. Large magnetic entanglement nanoparticles are undesirable as they are more likely to precipitate out of solution. Therefore, the nucleation nanoparticle shall be small enough to remain in solution. In one embodiment, the nucleation nanoparticle is generally spherical in shape with a diameter from about 0.5-1000 nm. Preferably, the nucleation nanoparticle is generally spherical in shape and has a diameter from about 1-100 nm.

Suitable stabilizers include, but are not limited to, polyethyloxazoline, polyvinylpyrollidinone, polyethyleneimine, polyvinylalcohol, polyethyleneglycol, polyester ionomers, silicone ionic polymers, ionic polymers, copolymers, starches, gum Arabic, suractants, nonionic surfactants, ionic surfactants, fluorocarbon containing surfactants and sugars. In one embodiment the stabilizer is a phenanthroline, bipyridine and oligovinylpyridine of the following formulas:

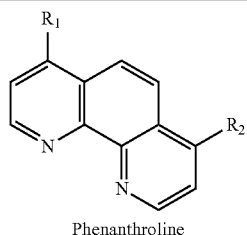

Phenanthroline

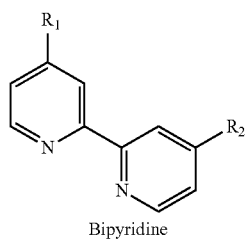

Bipyridine

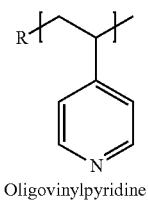

Oligovinylpyridine where $R_1$ is COOH, $CH_2OH$, $CH_2NH_2$, or $CH_2NHCH_3$; and $R_2$ is H, COOH, $CH_2OH$, $CH_2NH_2$, NH or $CH_2NHCH_3$.

In one embodiment where the magnetic entanglement nanoparticle contains palladium, these stabilizers link by acting as ligands for palladium ions and are therefore closely associated with the particle formation. In addition to linking, the stabilizers have hydrophilic groups that interact with the water phase. The linking and stabilization function of molecules such as phenathrolines in palladium particle formation is further described in Hainfeld, J. Structural Biology, 127, 177-184 (1999).

It is understood that particles derived from a broad class of materials (plastics, pigments, oils, etc) in water can be stabilized by a wide array of surfactants and dispersants that don't rely on specific coordination. These classes of stabilizers are also within the scope of this invention.

In one embodiment the stabilizer stabilizes the magnetic entanglement nanoparticle from precipitation, coagulation and minimizes the non-specific binding to random surfaces. In another embodiment, the stabilizer further functions as a nucleic acid binding element as described below.

Linker:

The linker is bound directly to the magnetic entanglement particle to allow the attachment of other intermediate connecting groups or target analyte binding elements. It is understood that the linker can also serve as a stabilizer or scaffold.

The linker can be bound through various binding energies. The total binding energy consists of the sum of all the covalent, ionic, entropic, Van der Walls and any other forces binding the linker to the catalytic nucleation nanoparticle. In one embodiment, the total binding energy between the linker and the magnetic entanglement particle is greater than about 10 kJ/mole. In another embodiment the total binding energy between the linker and the magnetic entanglement particle is greater than about 40 kJ/mole. Suitable linkers include, but are not limited to ligands, phenanthrolines, bidentates, tridentates, bipyridines, pyridines, tripyridines, polyvinylpyridines, porphyrins, disulfides, amine acetoacetates, amines, thiols, acids, alcohols and hydrophobic groups.

Scaffold Compositions:

The magnetic acid binding element may be connected directly to the catalytic nucleation particle or a linker. Alternatively, the nucleic acid binding element is attached to a scaffold, either individually or as a multiplicity. In either case, the final conjugate is endowed with the two essential properties—nucleic acid specific recognition-binding and an attached magnetic entanglement nanoparticle. Attaching the nucleic acid binding element to the scaffold may be by way of any of the common organic bonding groups such as esters, amides and the like.

Attachment to a common scaffold creates an enormous range of possible sizes, shapes, architectures and additional functions. In one embodiment the scaffold composition is a linear chain with the two functional groups at the ends. The chain itself can be of any composition, length and ionic character. In an alternative embodiment, often used in biological applications, polyethylene glycol with a reactive amine, acid or alcohol end groups is utilized as included in the following example.

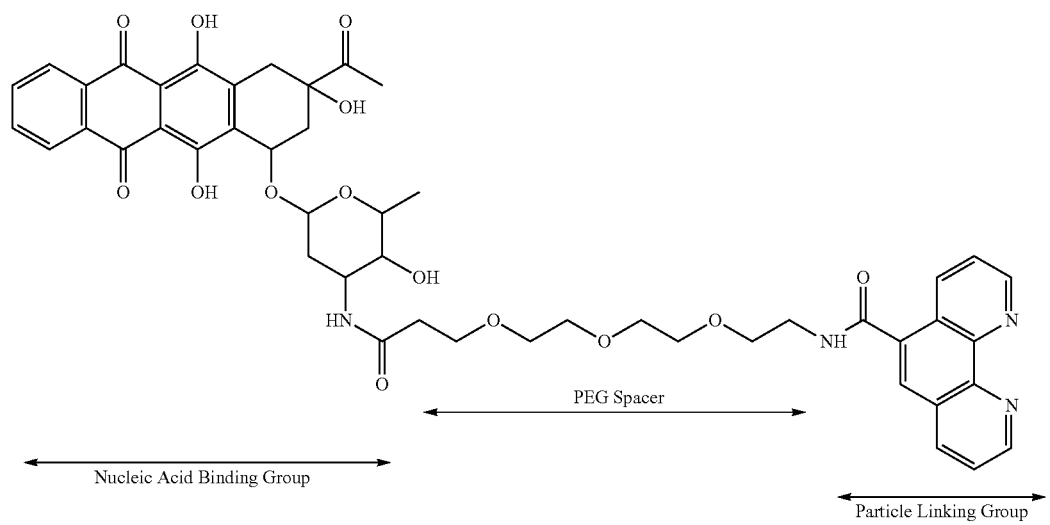 [SMILES: CC(=O)C1(O)Cc2c(O)c3c(c(O)c2C(OC2CC(NC(=O)CCOCCOCCOCCNC(=O)c4cc5cccnc5c5ncccc45)C(O)C(C)O2)C1)C(=O)c1ccccc1C3=O]
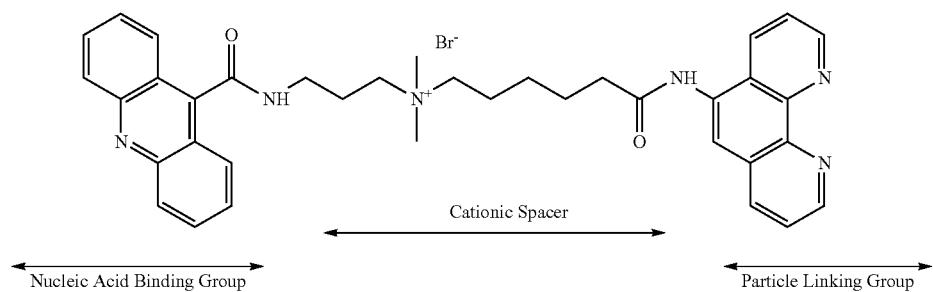
Linear short spacers with cationic character can be desirable as they can enhance intercalation performance.
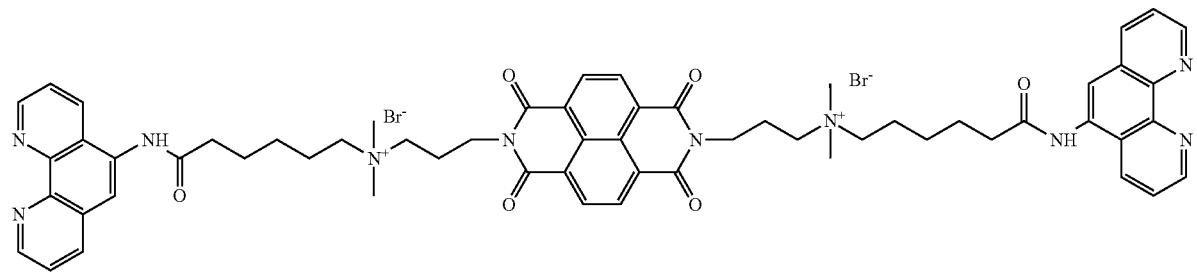
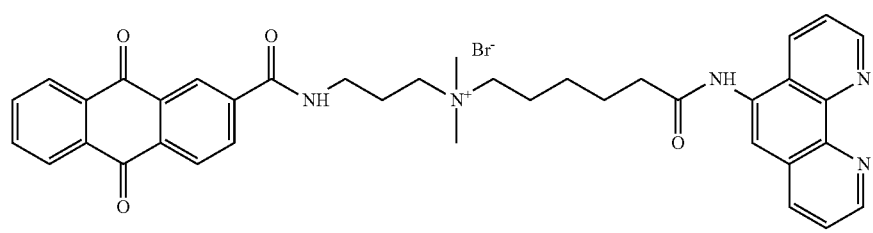

A polymeric or oligomeric scaffold allows for multiple groups to be joined in the same structure where the number of groups is limited only by the size of the chain.

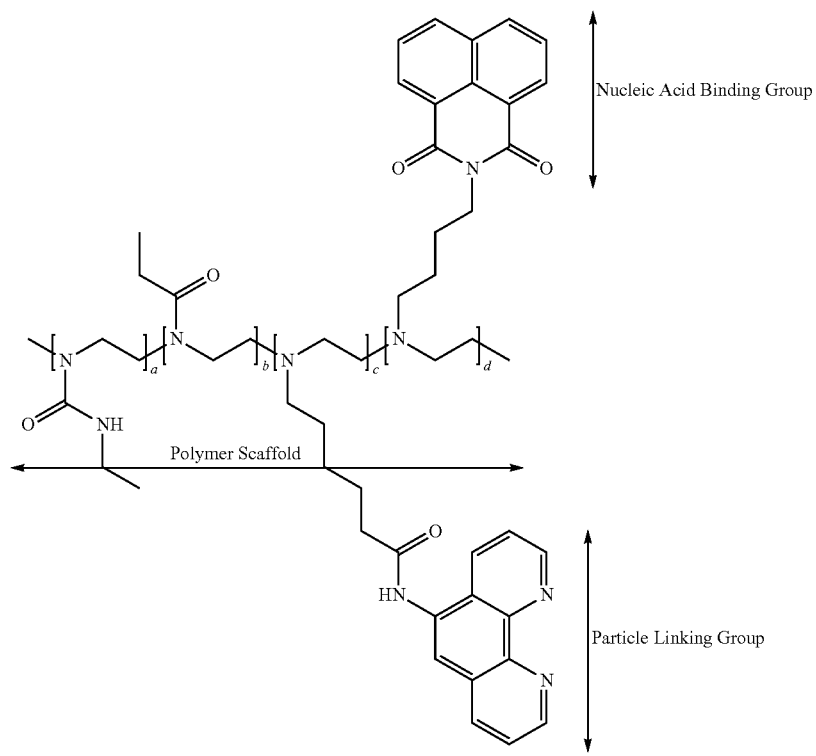

In addition to short and long chain structures scaffolds can be built with branched or very highly branched architectures. Furthermore, scaffolds can be a microgel particle with nanoparticles bound to a swollen polyvinylpyridine interior and peripheral nucleic acid binding elements are illustrated. In another embodiment the scaffold is a core-shell latex particle with nucleation nanoparticles centers and peripheral nucleic acid recognition groups populating the surface. It is understood that any scaffold compositions can be incorporated to connect intermediate connecting groups, catalytic nucleation nanoparticles or nucleic acid binding elements.

Steric Stabilizers:

In one embodiment a steric stabilizer is used to attach the target analyte binding element to the magnetic entanglement nanoparticle. The steric stabilizer is capable of functioning as a stabilizer, linker and scaffold as described above. In one embodiment the steric stabilizer is polyethylenimine, polyethyloxazoline or polyvinylpyrrolidone. The steric stabilizer binds to the magnetic entanglement particle with a total binding energy of at least 10 kJ/mole. In another embodiment the steric stabilizer binds to the magnetic entanglement particle with a total binding energy of at least 40 kJ/mole. The use of steric stabilizers eliminate any need for distinct stabilizers, linkers, or scaffolds. One or multiple nucleic acid binding elements can be attached to the steric stabilizer. Furthermore, one or multiple magnetic entanglement nanoparticles can be bound to the steric stabilizer.

Target Analyte Binding Substance:

In one embodiment for forming the target analyte binding substance on a nucleation nanoparticle, the nucleation nanoparticles are formed in solution with a stabilizer such as dimethyaminopyridine (DMAP). The stabilized nucleation nanoparticles are purified to retain clusters of the desired size. The nanoparticles are then treated directly with a nucleic acid binding element such as ethidium bromide or with a nucleic acid binding element connected to a linker or with a scaffold composition containing the nucleic acid binding element. The scaffold composition can be a polymer containing nucleic acid binding elements such as napthalimide or acridine. The polymer displaces some of the DMAP and attaches to the particle. It is understood that the nucleic acid binding element can be chemically attached to the scaffold composition prior to the attachment of the scaffold composition to the particle.

In another embodiment for forming the target analyte binding substance on a nucleation particle, the nucleation nanoparticles are formed in solution in the presence of a nucleic acid binding element such as ethidium bromide or in the presence of a nucleic acid binding element connected to a linker or in the presence of a scaffold composition containing the nucleic acid binding element. The scaffold composition can be a polymer containing nucleic acid binding elements such as napthalimide or acridine. It is understood that the nucleic acid binding substance connects to the particle during the particle formation process and may offer some colloidal stability to the dispersion. In addition, stabilizers in the form of ionic surfactants, non ionic surfactants, water soluble oligomers and polymers may also be added to enhance colloid stability and control particle size.

Referring to FIGS. 4A-4D there are shown various views of one embodiment of the cartridge body 102. It is understood that various designs can be used to house the reservoir insert. The cartridge body 102 has an inner cylindrical surface 140. The inner cylindrical surface 140 houses the reservoir insert (not shown). The inner cylindrical surface 140 is smooth to allow the reservoir insert to freely rotate. The cartridge body is constructed from any material that is both ridged enough to support the cartridge body and smooth enough to allow for rotation of the reservoir insert. In one embodiment, the inner cylindrical surface 140 has a slight taper to facilitate attachment of the reservoir insert (not shown) having an outer cylindrical surface with a slight taper.

In one embodiment the cartridge body has a syringe molding 141. Although only one syringe is shown it is understood that a plurality of syringes can be used. The syringe molding 141 is capable of housing a plunger. The plunger draws and pushes fluids through the reservoir inserts fluid paths. In one embodiment the plunger 144 is retained within the syringe molding 141. Optionally, the cartridge body has a reaction chamber 142 and sensor mount 143. The sensor mount 143 is capable of holding a sensor board. The sensor board is aligned to the sensor mount 143 by the alignment posts 146. The plunger delivers fluids through the fluid paths and to the reaction chamber 142. The fluids chemically react with other fluids or devices in communication with the reaction chamber 142. It is understood that a fluid output can be attached to the cartridge body to allow the fluid to transfer from the rotating valve to a desired location. Furthermore, a fluid input allows the introduction of fluids to the rotating valve. While a plunger has been described in this embodiment, it is understood that any suitable fluid delivery device could be substituted to effectively transfer fluids within the cartridge.

In one embodiment the sensor board contains a chip having a reactive surface. The chip is positioned such that it is in communication with the reaction chamber 142. In one embodiment the chip forms one side of the reaction chamber 142. Fluid flows into the reaction chamber 142 and contacts the reactive surface of the chip (not shown). The chip is in electrical communication with a detection device to provide readings and results of the testing.

Figure 5A:
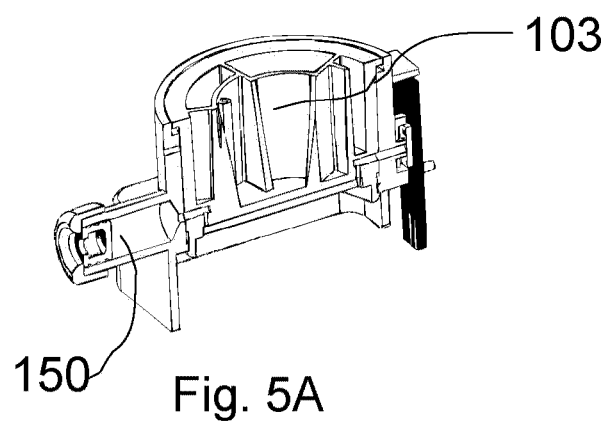
FIGS. 5A-5B show a cross-sectional view of an assembled rotating valve according to one embodiment having the multi-chamber reservoir secured in the cartridge body.
Figure 5B:
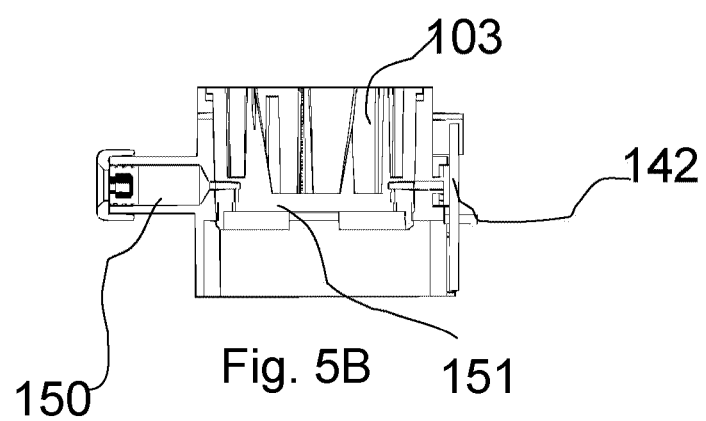
Figure 6A:
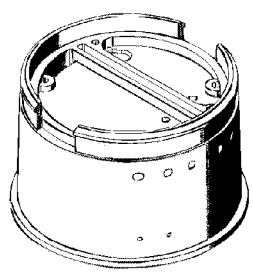
FIGS. 6A-6G show a graphical representation of the multi-chamber reservoir according to one embodiment.
Figure 6B:
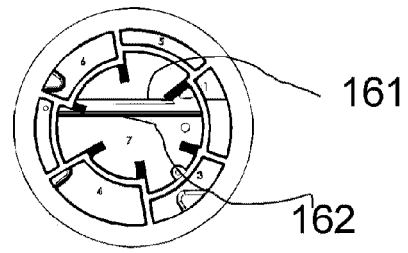
Figure 6C:
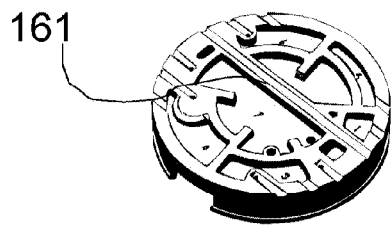
Figure 6D:
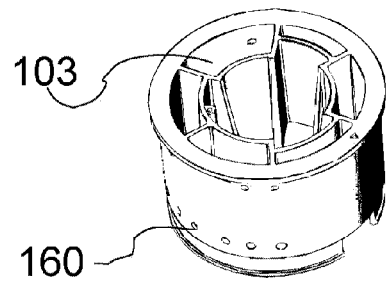
Figure 6E:
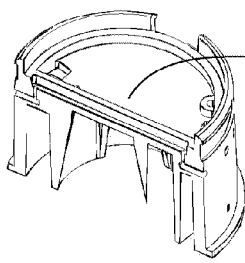
Figure 6F:
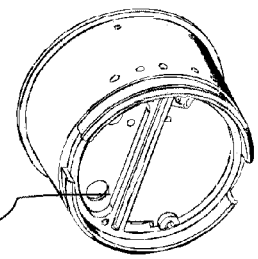
Figure 6G:
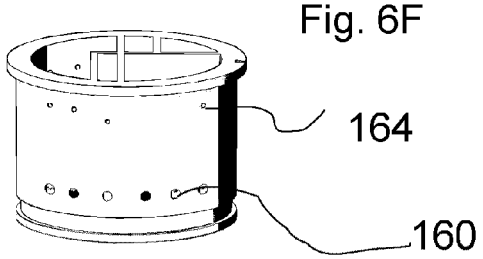

Referring to FIGS. 5A-5B there is shown a cross sectional view of an assembled rotating valve having a plunger 150. The plunger 150 is capable of drawing fluid from the reservoirs 103. Once the plunger 150 draws the fluid, the rotating valve repositions the fluid path to align a distinct port with the syringe molding. The plunger 150 then pushes the fluid through the fluid path 151 into the reaction chamber 142, a different reservoir, or a pre-treatment chamber.

Referring to FIGS. 6A-6G there are shown multiple views of the reservoir insert. The reservoir insert has an outer cylindrical surface 106. In one embodiment the outer cylindrical surface 106 is tapered. The reservoir insert contains multiple reservoirs 103. The reservoirs 103 can contain samples, standards, wash, catalyst or any other desirable fluid. In one embodiment the reservoirs 103 include a waste reservoir to discharge fluids. The reservoir insert further contains multiple ports 160. Each port 160 has a unique fluid path. Each chamber and reservoir has a fluid path that is in communication with a port to transfer fluid to or from the chamber or reservoir. A syringe molding on the cartridge body (not shown) lines up with a port to extract or push fluid. To prevent pressure differentials from forming pressure relief ports 164 are positioned along the reservoir insert. In addition to the unique fluid paths, the reservoir insert contains at least one fluid through channel 161. The fluid through channel 161 allows for the fluid to flow from the one end of the reservoir insert to the other. For example, the fluid can flow from the syringe molding to the reaction chamber of the cartridge body (not shown).

To prevent fluid interaction in the fluid through channel 161 a plurality of fluid through channels are used. The secondary fluid through channel 162 is used to prevent early reactions or other adverse fluid interactions. In one embodiment the reservoir insert contains a heater contact region 163. The heater contact region is positioned below the reservoirs for which it is desirable to heat the fluid in the reservoir. Furthermore, the heater is capable of heating the fluid through channel 161.

Figure 7A:
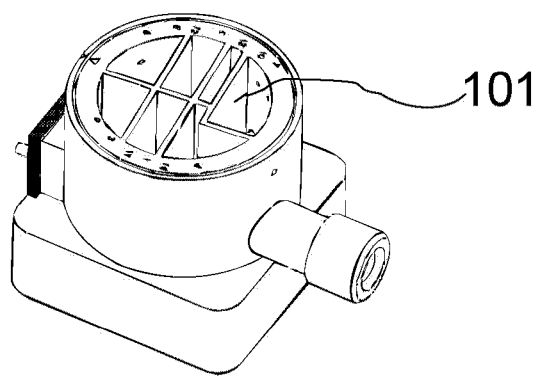
FIGS. 7A, 7B, 8A, 8B, 9A, 9B, 10A, 10B, 11A, 11B, 12A, 12B, 12C, 13A, 13B, 14A, 14B, 14C, 15A, 15B, 16A, 16B and 16C show various graphical representations of an assembled rotating valve with the multi-chamber reservoir positioned for desired fluid flow through the channels according to one embodiment.
Figure 7B:
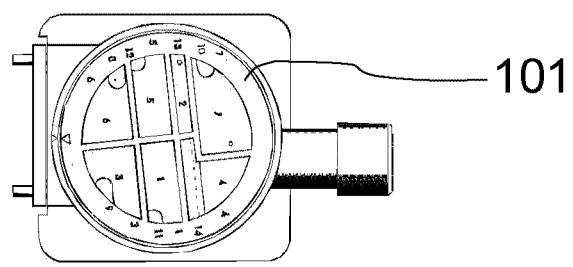

Referring to FIGS. 7A-16C there are shown multiple of views of an assembled rotating valve rotated in various positions. As shown in FIGS. 7A-7B the reservoir insert 101 is in a closed position. No ports are in line with the syringe molding (not shown). This prevents any leakage of fluid from the reservoir. In one embodiment at least one reservoir is a sample reservoir. The sample reservoir enables the user to inject a fluid sample into the reservoir through the heat film seal. In one embodiment the sample reservoir contains disrupting objects, such as glass beads, to assist in breaking down samples into testable nucleic acid strands.

Figure 8A:
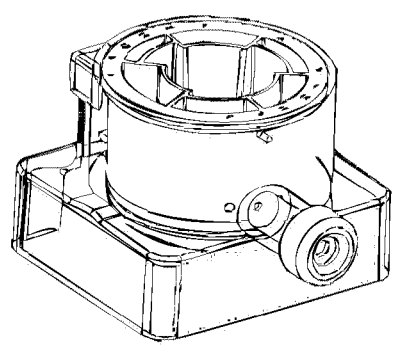
Figure 8B:
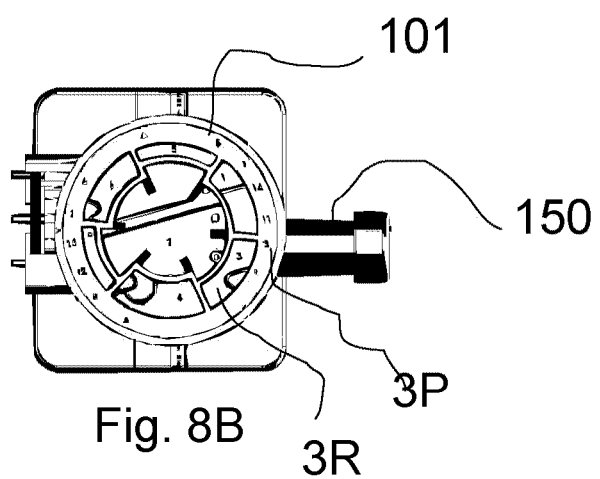
Figure 9A:
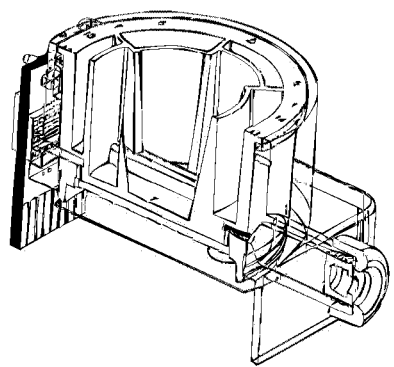
Figure 9B:
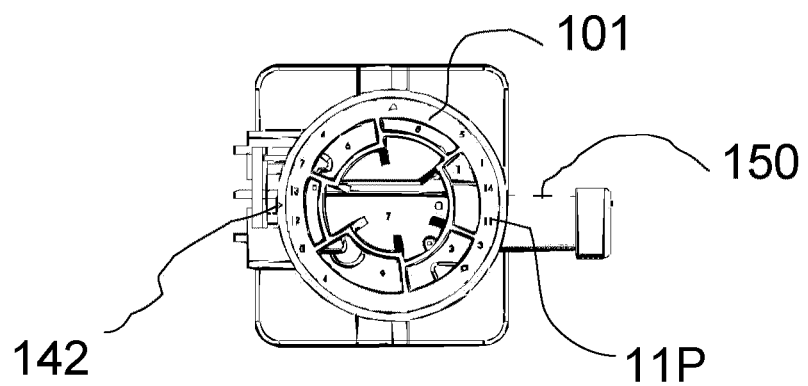

Referring to FIGS. 8A-8B the reservoir insert 101 is positioned such that port 3 is in-line with the syringe molding. Once positioned fluid from reservoir 3 can be drawn through port 3 and into the syringe molding 141. Once fluid is pulled from a reservoir, and no additional fluid is required from that reservoir, that reservoir can be used as an alternative reservoir for waste storage. Referring to FIGS. 9A-9B, the reservoir insert 101 is positioned such that port 11 is in-line with the syringe molding. The plunger pushes the fluid drawn from reservoir 3 into port 11 and the fluid passes to the reaction chamber 142.

Figure 10A:
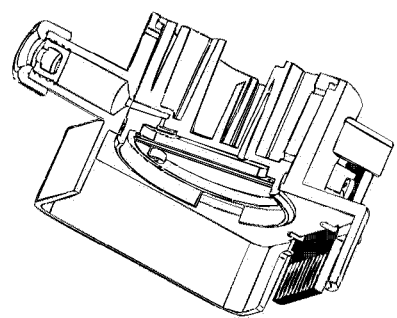
Figure 10B:
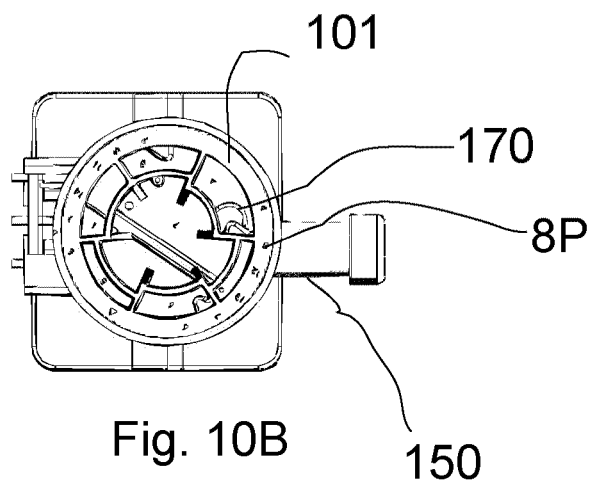
Figure 11A:
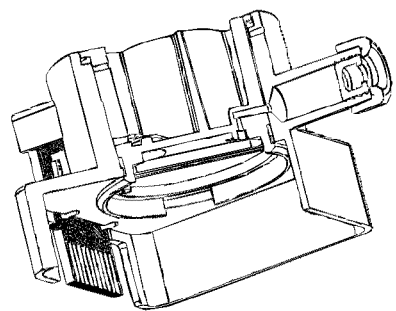
Figure 11B:
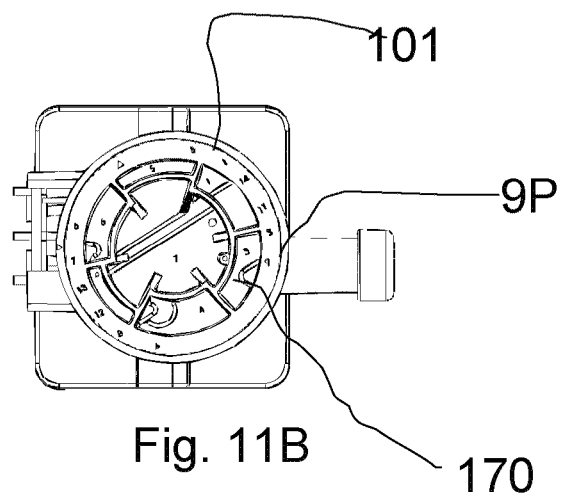

Referring to FIGS. 10A-10B the reservoir insert 101 is positioned such that port 8 is in-line with the syringe molding. In one embodiment fluid is pushed from the syringe molding 141 into port 8 and into a heating chamber. Once in the heating chamber 170 the fluid is heated at the desired temperature for a predetermined amount of time. Once the heating has completed the fluid is drawn back into the syringe molding. It is understood that the fluid may be drawn through the same port 8 or unique port in communication with the heating chamber. As shown in FIGS. 11A-11B the fluid is drawn into the syringe molding from a unique port 9 in communication with the heating chamber 170.

Figure 12A:
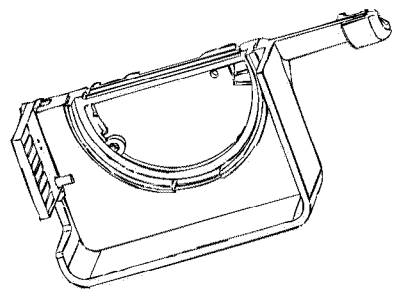
Figure 12B:
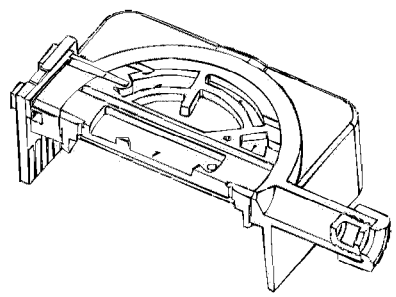
Figure 12C:
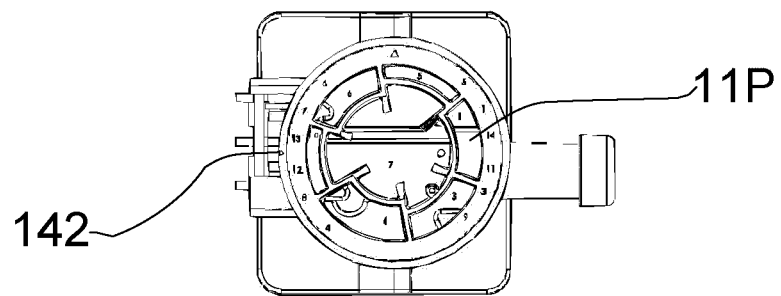

Referring now to FIGS. 12A-12C there is shown the flow through fluid path 161 from the syringe molding to the reaction chamber 142. In this embodiment the flow through fluid path corresponds with port 11.

Figure 13A:
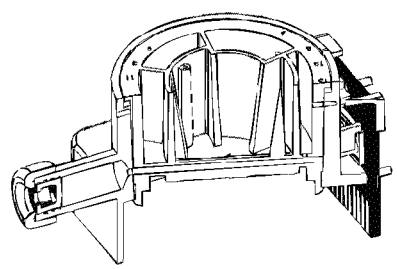
Figure 13B:
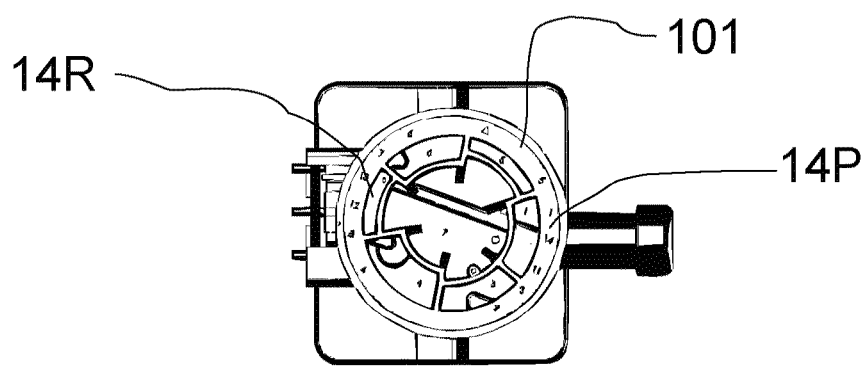
Figure 14A:
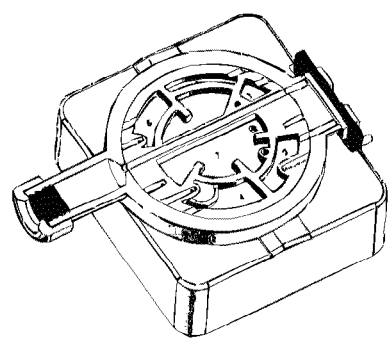
Figure 14B:
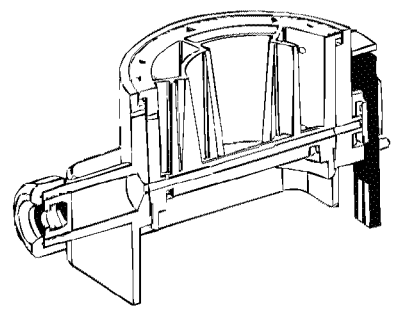
Figure 14C:
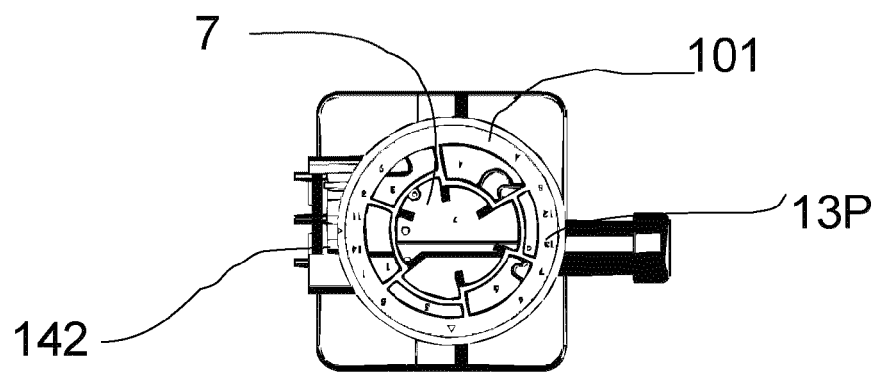

Referring to FIGS. 13A-13B there is shown the reservoir insert 101 positioned such that port 14 is in-line with the syringe molding. Reservoir 14 is in communication with port 14. The fluid contained in reservoir 14 is pulled into the syringe molding. The reservoir insert 101 then rotates to port 13 as shown in FIGS. 14A-14C. The fluid from reservoir 14 is then pushed through port 13 to the reaction chamber 142. The fluid passes through a channel that is distinct from the channel associated with port 11. This prevents fluids from coming in contact with and reacting with each other while in the channels. The fluids first come into contact in the reaction chamber 142.

After the desired reaction time the plunger pushes the fluid from the reaction chamber 142 into the waste reservoir 7. The plunger draws the fluid back through port 11 and the reservoir insert rotates to a port in communication with waste reservoir 7. The plunger then pushes the fluid into the waste reservoir 7. It is understood that after use any reservoir can be utilized as a waste reservoir. In an alternative embodiment, the plunger stops pushing fluid once it reaches the reaction chamber 142. Upon completion of the reaction time, the plunger continues to push the fluid through the reaction chamber and into a port in communication with a waste reservoir or separate archive reservoir. An archive reservoir stores sample for additional testing or verification.

Figure 15A:
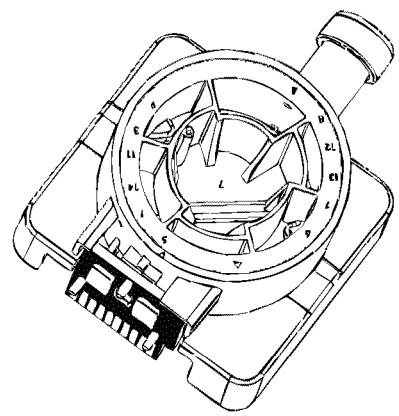
Figure 15B:
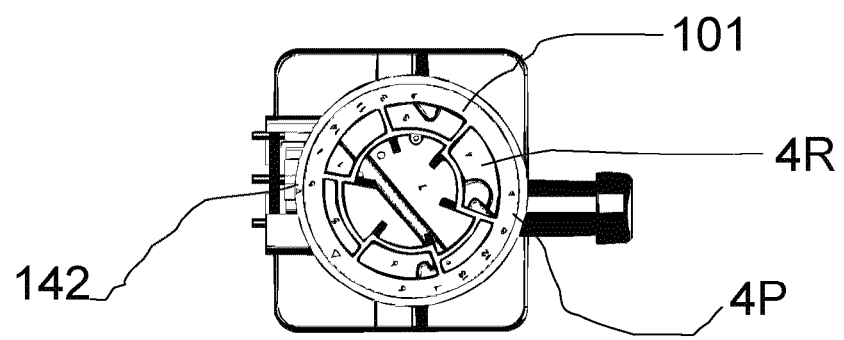
Figure 16A:
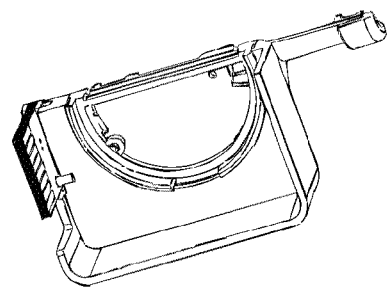
Figure 16B:
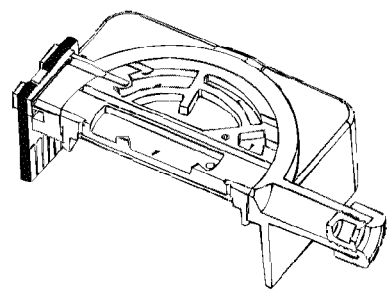
Figure 16C:
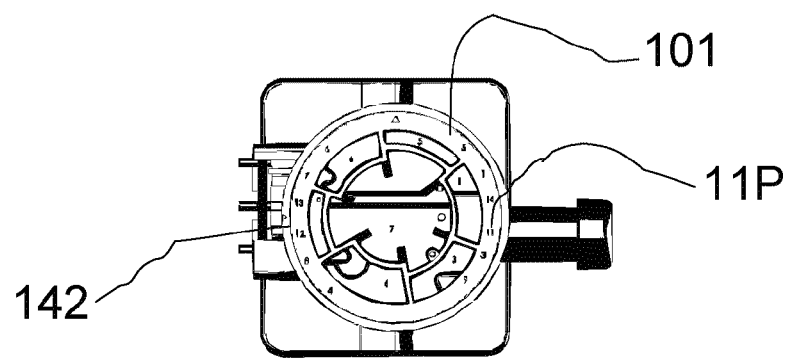

Referring to FIGS. 15A-15B there is shown the reservoir insert 101 positioned such that port 4 is in-line with the syringe molding. Port 4 is in communication with reservoir 4 containing a flush fluid. The flush fluid is drawn from reservoir 4 through port 4 and into the syringe molding. The reservoir insert 101 rotates to port 11 and the plunger pushes the flush fluid into port 11 and to the reaction chamber 142 as shown in FIGS. 16A-16C.

Once completed the rotating valve can be removed and disposed. A fresh rotating valve with the same or unique fluids is then inserted into the detection device.

Figure 17:
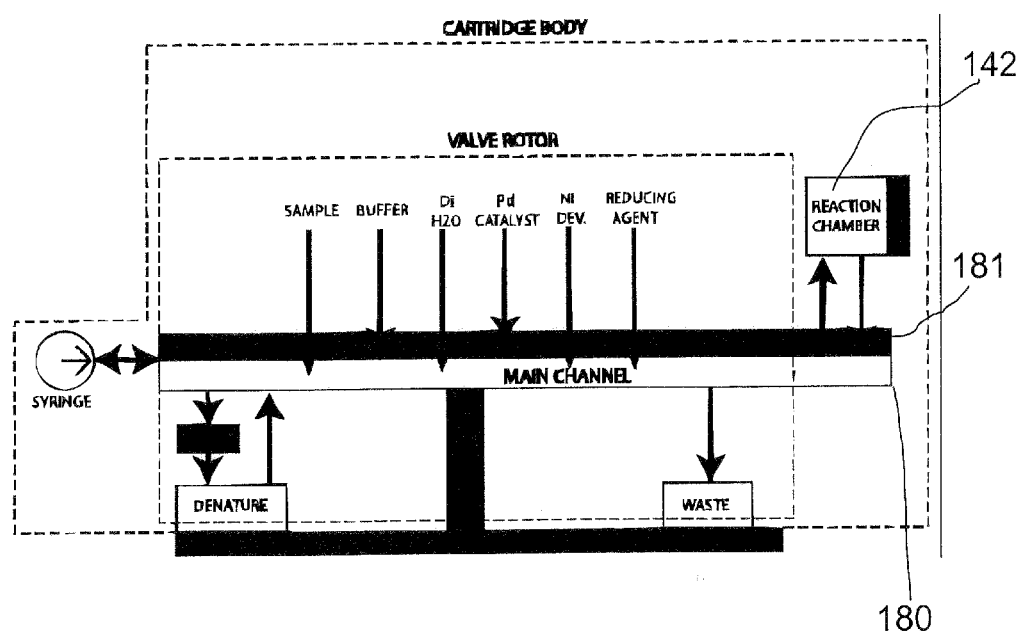
FIG. 17 shows a schematic representation of the rotating valve according to one embodiment.

Referring to FIG. 17 there is shown a schematic of a rotating valve of one embodiment. The reservoir insert contains six fluids in various reservoirs. Five fluids pass from their respective reservoirs into the syringe molding and through the main channel 180 into the reaction chamber 142. One fluid passes from the syringe molding through a secondary channel 181 and into the reaction chamber 142 to prevent any contamination or premature reactions.

Figure 18:
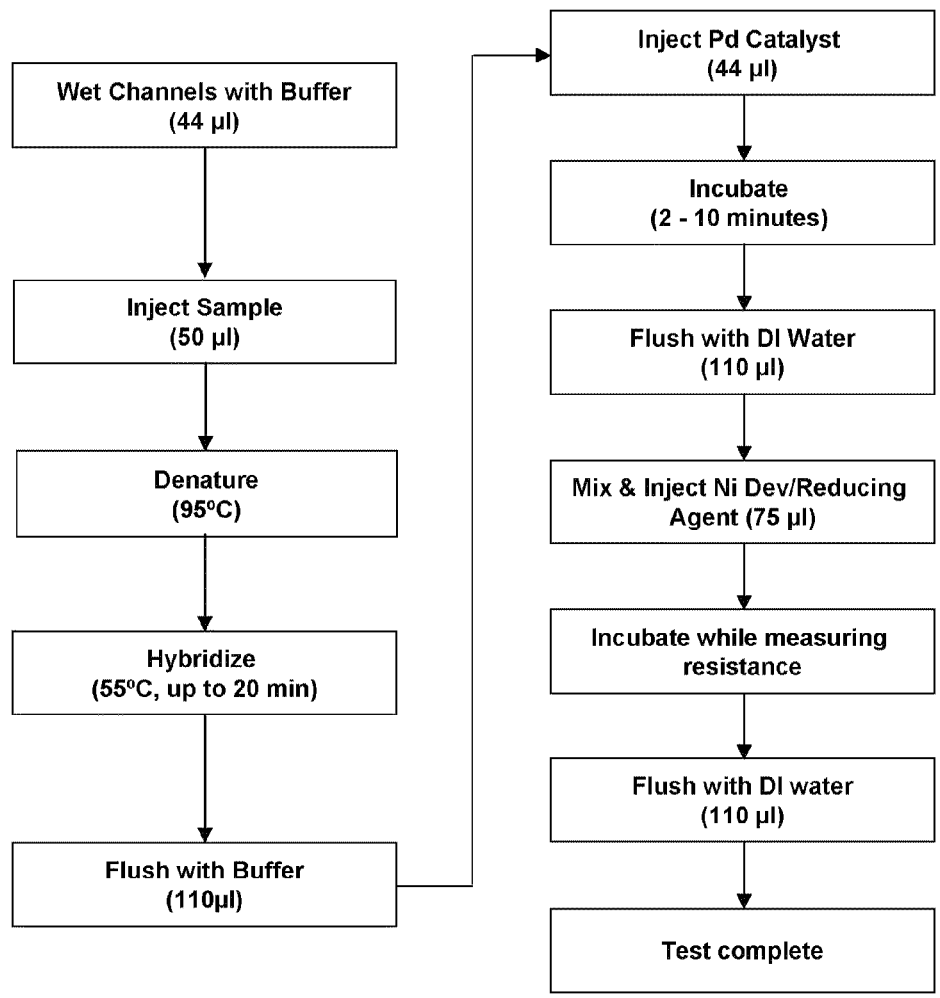
FIG. 18 shows a process flow chart for one use of the rotating valve according to one embodiment.

Referring to FIG. 18 there is shown a process flow according to one embodiment. Once a sample is injected into the sample reservoir and the detection device is activated the testing begins. The channels are first preconditioned with a small amount of buffer. The sample is then transferred from the sample reservoir to the heating reservoir and heated at 95° C. for 5 minutes. The heated sample is then transferred to the reaction chamber to hybridize for 20 minutes. The hybridization process enables the sample to chemically bond with biological probes found on the chip in communication with the reaction chamber. The biological probes specifically bind to target nucleic acid molecules found in the sample as described in U.S. Pat. No. 6,399,303 issued to Connolly on Jun. 4, 2002, which is hereby incorporated by reference. It is understood that a single chip may contain a plurality of distinct and redundant biological probes to increase sensitivity and to test for a variety of target nucleic acid molecules. It is further understood that the rotating valve can be used in any system requiring the manipulation and transport of a plurality of fluids.

After hybridization the sample is flushed with buffer to remove any excess compounds. Optionally a catalyst such as palladium is transferred to the reaction chamber and allowed to incubate for 10 minutes. The remaining catalyst is then flushed with water. A mixture of a reducing agent and metal, such as nickel, are pushed into the reaction chamber. The metal coats the target sample creating a conductor on the chip. The excess non-bonded metal is flushed with water. The resistance across biological probes bonded together by a target sample coated in metal dramatically reduces, indicating the presence of the target sample. The detection device writes the results of the test and the test is complete.

Figure 19A:
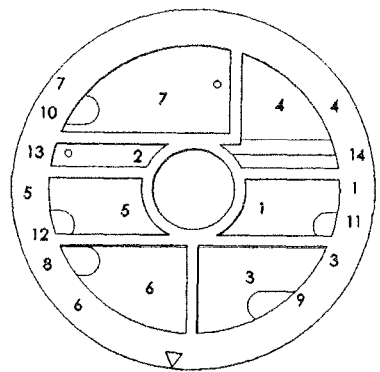
FIGS. 19A, 19B, 20A, 20B, 21A and 21B show a graphical representation of multi-chamber reservoir insert configurations according to various embodiments.
Figure 19B:
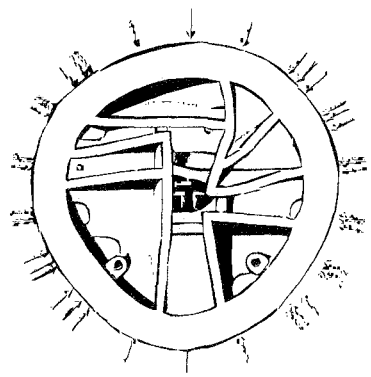

Referring now to FIGS. 19A-19B there is shown a variations of the reservoir insert. The chambers of the insert are shown in a rectangular configuration. Changes to the chamber sizes and shapes can be performed to optimize the particular reagent and waste chambers.

Figure 20A:
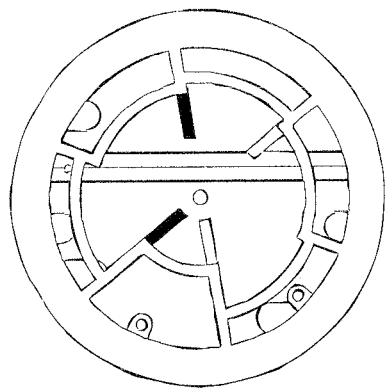
Figure 20B:
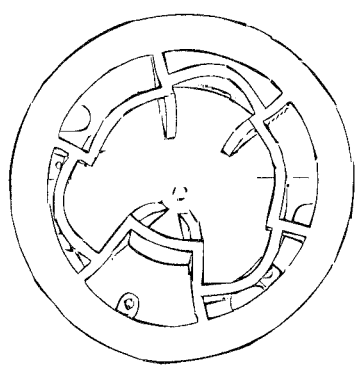

Referring now to FIGS. 20A-20B there are shown variations of the reservoir insert. The chambers of this embodiment are shown to have radial chambers. In one embodiment the chambers are of uniform size and shape around the radius of the insert.

Figure 21A:
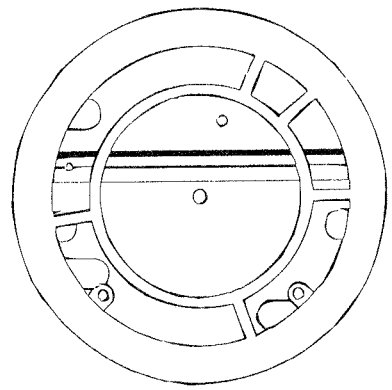
Figure 21B:
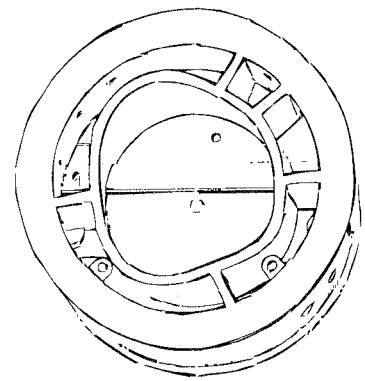

Referring now to FIGS. 21A-21B there are shown variations of the reservoir insert. The chambers are of various sizes along the radius of the insert to house differing amounts of reagents within each chamber. While variations of the insert are shown in the various embodiments, it is understood that any variation of the reservoir insert containing a plurality of ports and reservoirs can be used.

Figure 22:
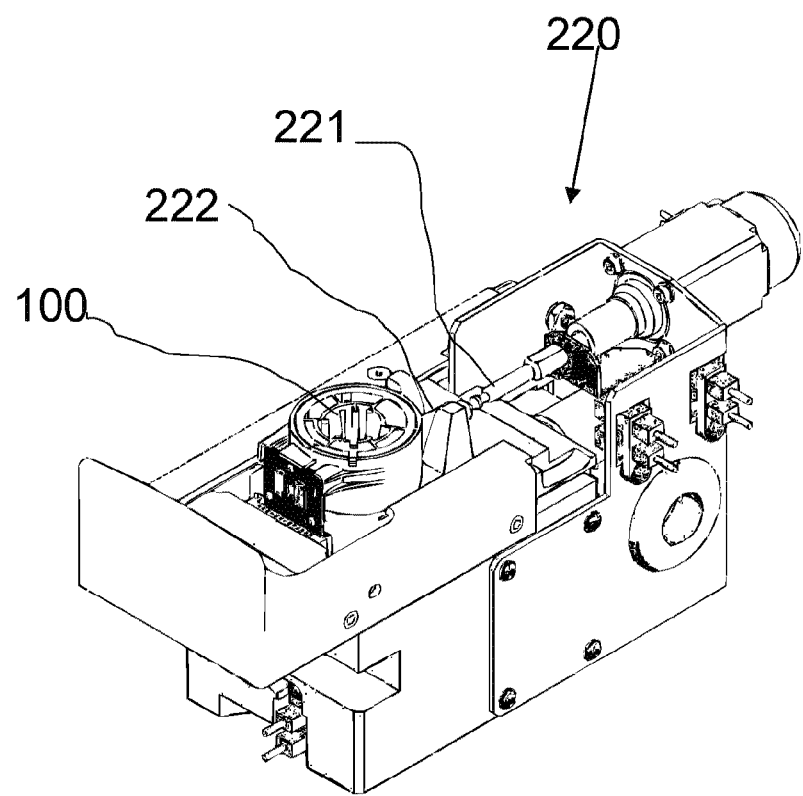
FIG. 22 shows a graphical representation of sampling device containing a rotating valve drive and plunger drive according to one embodiment.

Referring to FIG. 22 there is shown a sampling device having a rotating valve drive and a plunger drive. The rotating valve 100 sets on top of the rotating valve drive. The plunger drive 220 contains a long cylindrical section 221 having a tip 220. The tip 220 connects to the plunger inside of the syringe molding 141. In one embodiment the tip 220 is conical improve contact with the plunger. The plunger drive moves the cylindrical section 221 axially causing the plunger to either pull or push fluids from the reservoirs in the rotating valve 100.

Figure 23:
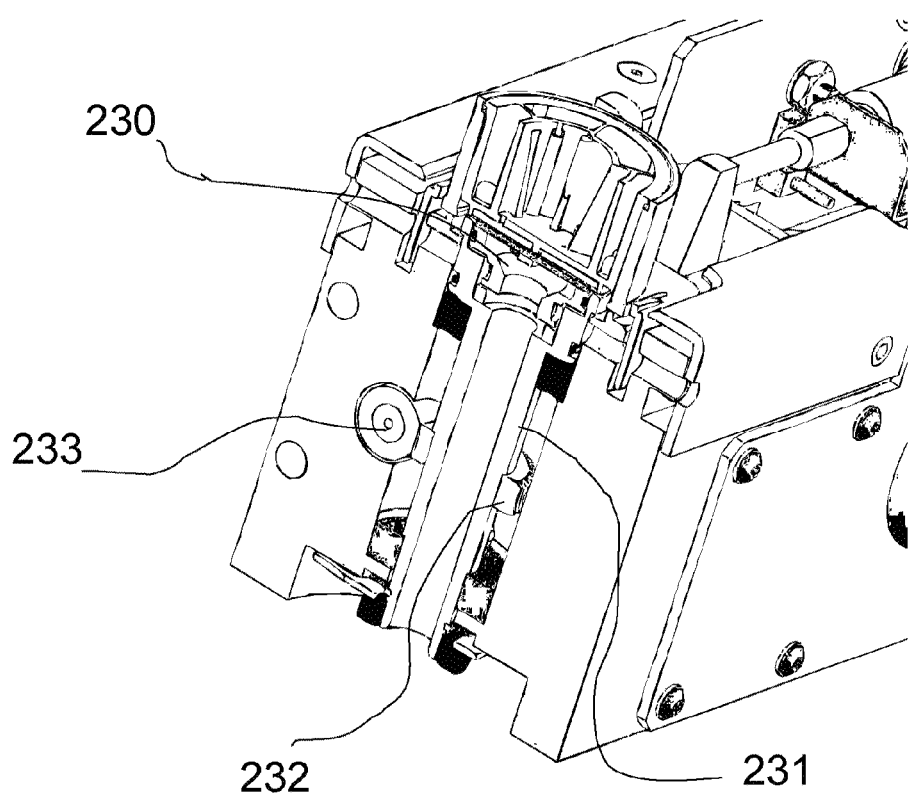
FIG. 23 shows a graphical representation of a rotating valve drive with the rotating valve removed according to one embodiment.

Referring to FIG. 23 there is shown the rotating valve drive according to one embodiment. The rotating valve sets atop the contact surface 230. The contact surface 230 then rotates to position the reservoir insert to the desired location within the rotating valve. In one embodiment the contact surface 230 is part of a drive assembly 231. A worm gear 232 is attached to the drive assembly 231. A worm drive 233 engages the worm gear 232 causing the drive assembly 231 to rotate. It is understood that any suitable means to rotate the reservoir insert can be employed.

Figure 24:
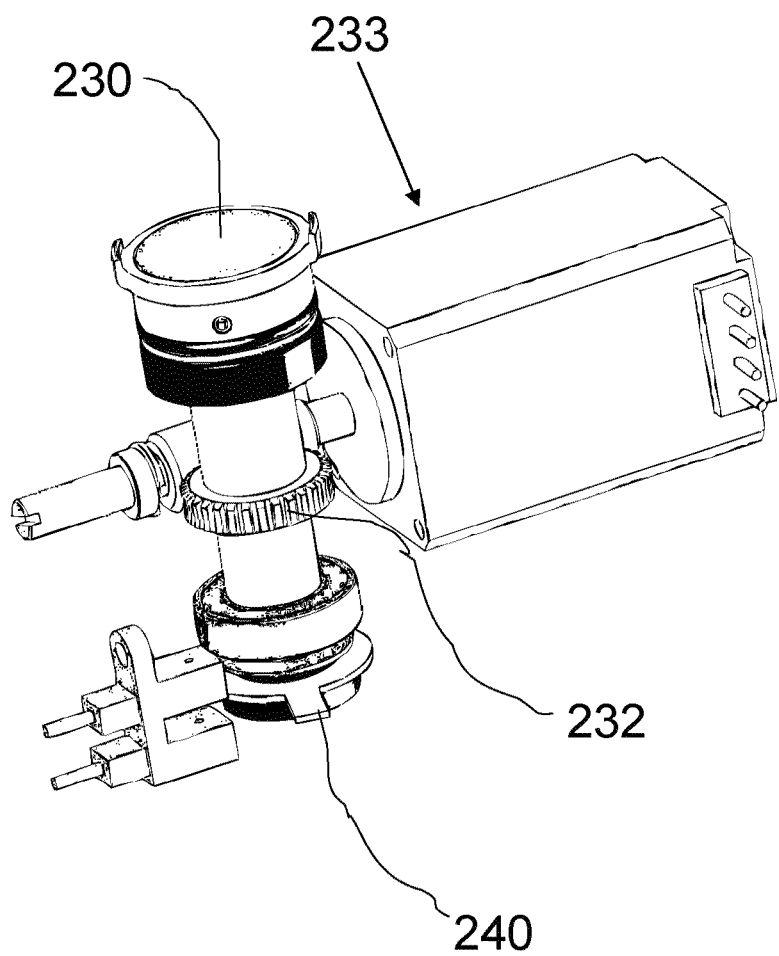
FIG. 24 shows a graphical representation of the stepper motor assembly and worm drive according to one embodiment.

Referring to FIG. 24 there is shown another view of the rotating valve drive. The worm drive 233 is a stepper motor positioned to advance the worm gear 232. A home flag 240 is attached to the drive assembly to zero the device. At any time during fluid sampling the home flag can be zeroed allowing the worm drive 233 to advance the appropriate distance.

Figure 25:
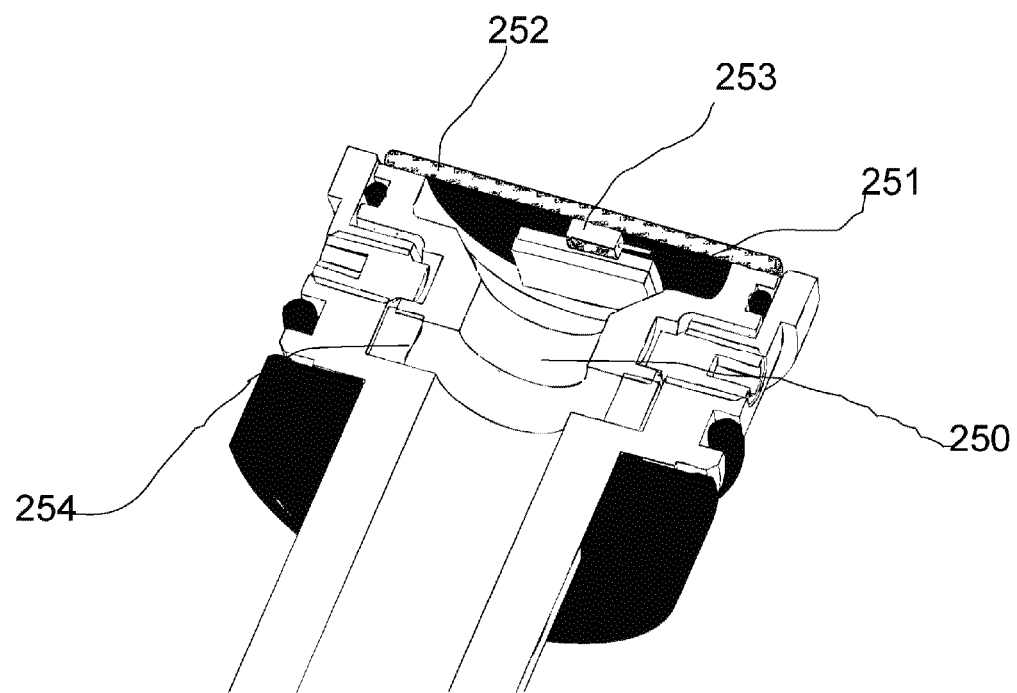
FIG. 25 shows a graphical representation of a the heater according to one embodiment.

Referring to FIG. 25 there is shown the contact surface having a heater. The contact surface is spring loaded to improve contact with the rotating valve. At least one spring 254 is positioned to allow movement of the contact surface. In one embodiment the contact surface contains a heater mount 250 to mount the heating elements. At least one resistor 251 is positioned on the heater mount 250. A heating plate 252 transfers heat from the resistors through the heating plate 252 and to the desired location on the rotating valve. In one embodiment the heating plate is an aluminum heating plate. Optionally, a temperature sensor 253 is positioned near the resistor or heating plate to detect the applied temperature. It is understood that the contact surface (not shown) can be positioned over the heater plate. The contact surface is made from a material that allows an efficient thermal transfer from the heating plate to the rotating valve.

EXAMPLES

Sonication Bead Disruption

Spores were prepared and isolated from *Bacillus subtilis* from sporulation media+. To a 100 ul aliquot of the spores taken from the culture, an equal volume of 0.1 mm glass beads were added in a microfuge tube. The tip of the microfuge tube was placed in the socket of a Branson Ultrasonic sonicator. Using a power setting of 2, the beads within the tube were agitated for two minutes. Afterwards, gram staining showed that greater than 90% of the spores were disrupted by this process. This was confirmed with plating assays by counting colonies formed from spores surviving the process. Estimation of the amount of DNA released was accomplished by spotting an aliquot of the lysate onto the surface of a 1% agarose gel containing 1 mg/ml ethidium bromide. A Bio-Rad Fluor-S imager compared the intensity of the sample fluorescence against known standard amounts of DNA also spotted onto the gel surface. Using this technique, approximately 10 ng of DNA can be isolated from $2.5 \times 10^5$ spores.

Magnetic Examples

Metal salts (nickel, cobalt, iron) with a small amount of palladium salt are dissolved in a solvent (water and/or polar organic solvent) along with a stabilizer (phenanthroline, bipyridine, polyvinylpyrrolidinone). A reducing agent is added (dimethylamineborane, sodium borohydride) and the mixture is held until the metal clusters are formed. If needed, solvents and excess salts can be removed by centrifugation, decantation, washing, and resuspension of the metal clusters.

Solution A—24 g of nickel chloride hexahydrate and 44 g of sodium citrate were dissolved in 500 ml of water.

Solution B—24 g of ethanolamine were dissolved in 500 ml of water.

Solution C—5 g of cobalt chloride hexahydrate were dissolved in 100 ml water.

Solution D—2 g of potassium tetrachloropallidate and 6 g of potassium chloride were dissolved in 100 ml of water.

Solution E—1 g of bathophenanthroline-disulfonic acid, disodium salt hydrate was dissolved in 100 ml water.

Solution F—3 g of dimethylamine borane were dissolved in 100 ml water.

Magnetic Example 1

In a 20 ml glass vial, 1 ml solution A and 1 ml of solution B were mixed. 0.1 ml of solution D was added, followed immediately by 0.2 ml of solution E. Then 0.5 ml of solution F was added and the mixture was held at 60 degrees C. for 30 minutes. After cooling to room temperature, the mixture was placed in a strong magnetic field for 10 seconds (the magnetic field was from the permanent magnetic removed from a discarded computer hard drive) and it was observed that most of the metal clusters moved to the wall of the vial nearest the magnet.

Magnetic Example 2

In a 20 ml glass vial, 0.2 ml solution A, 0.8 ml solution C and 1 ml of solution B were mixed. 0.1 ml of solution D was added, followed immediately by 0.2 ml of solution E. Then 0.5 ml of solution F was added and the mixture was held at 60 degrees C. for 30 minutes. After cooling to room temperature, the mixture was placed in a strong magnetic field for 10 seconds (the magnetic field was from the permanent magnetic removed from a discarded computer hard drive) and it was observed that most of the metal clusters moved to the wall of the vial nearest the magnet.

Preparation of Magnetite Clusters Example

A first solution of ferric chloride (0.8M), ferrous chloride (0.4M) and hydrochloric acid (0.4M) was mixed and 0.2 micron filtered. A second solution was prepared with 72 ml of ammonium hydroxide (30%) with water to make 1 liter.

1 ml of the ferric/ferrous chloride solution was added with stirring to 20 ml of the ammonium hydroxide solution. Stirring was continued for 15 seconds. The solution (in a 20 ml vial) was placed on a strong magnet and allowed to stand for 1 minute, after which all the product was pulled to the bottom of the vial. The clear supernatant liquid was decanted, replaced with water, mixed, and placed near the magnet. Again the product was pulled to the bottom of the vial. This process was repeated three times to wash the product free from any residual ammonium and iron salts. The vial was then filled with 20 ml of water and ultra-sonicated for 5 minutes at 4 watts power. The suspension was then filtered through a 1 micron glass filter to give a stable suspension of magnetite particles that remain in suspension until pulled down by magnetic forces or centrifugation.

Attachment of Magnetic Particles Example

Nucleic acid molecules were purified from fruit flies, then lysed with ferrite particles followed by magnetic separation and elution. The magnetic beads captured more than 90% of available nucleic acid molecules.

Hybridizing to Capture Probes Example

Once the nucleic acid molecules are prepared, they are hybridized to capture probes on sensor electrodes. Samples of nucleic acid molecules from *Bacillus* cells were prepared through ultrasonic lysis and magnetic concentration. The eluted DNA was bound to probes on the sensor chip to demonstrate that there are no inhibitors of hybridization.

Sample Cleaning

In one embodiment, the sample is cleaned to remove compounds which could potentially inhibit the binding of nucleic acid molecules to sensors. By attaching magnetic particles to the sample and manipulating the sample with a magnetic field the sample is both concentrated and cleaned from impurities.

Cleaning Example

Bacterial and spore samples mixed with soil were processed to evaluate complex samples. Soil is a complex medium which is known to inhibit PCR-based systems. Soil was added to samples containing six whole fruit flies. The flies are intended to represent insects that might be evaluated for carrying a disease like malaria. Up to 320 micrograms of the soil were added per milliliter of sample. The fruit flies were lysed and the DNA and RNA were captured using ferrite particles with the addition of ethanol. The particles were collected magnetically, washed with buffer and ethanol to remove contaminants then concentrated with magnetics. The nucleic acid molecules were then eluted in hybridization buffer at 90° C. to denature the DNA component. The ferric particles worked well in the presence of soil. Minimal loss was seen until the level of soil in the sample reached 32 milligrams per 100 micro liters where the solution becomes viscous and particle movement is difficult.

DNA from Complex Samples Example

*Bacillus* cells were mixed with cattle ear tissue or whole fruit flies and the mixtures were taken through the sample preparation process. The resulting nucleic acids were hybridized to probes on sensor chips. The chips were then treated with YOYO-1 dye to detect hybridized DNA. The target DNA sequences in the cells hybridized to the sensor chips at levels comparable to *Bacillus* cells processed separately. Negative controls without *Bacillus* showed no hybridized DNA. The experiment was repeated with dirt added to the samples as described above. Hybridization efficiency remained at least 60% of the hybridization seen in the sample without eukaryotic cells and dirt.

Washing Particles with a Flow Example

Magnetic particles were bound to DNA and then the solution introduced into a clear plastic tube with a 2 mm diameter.

A magnet was placed under the center of the tube. A wash buffer was pushed through the tube using a syringe pump. The particles visually remained in place through the washing. After washing the magnet was removed and the particles were rinsed out of the tube. DNA was eluted at high temperature and run on a gel. No apparent loss of DNA was observed.

Efficiency of Binding and Release of Magnetic Particles Example

Figure 29:
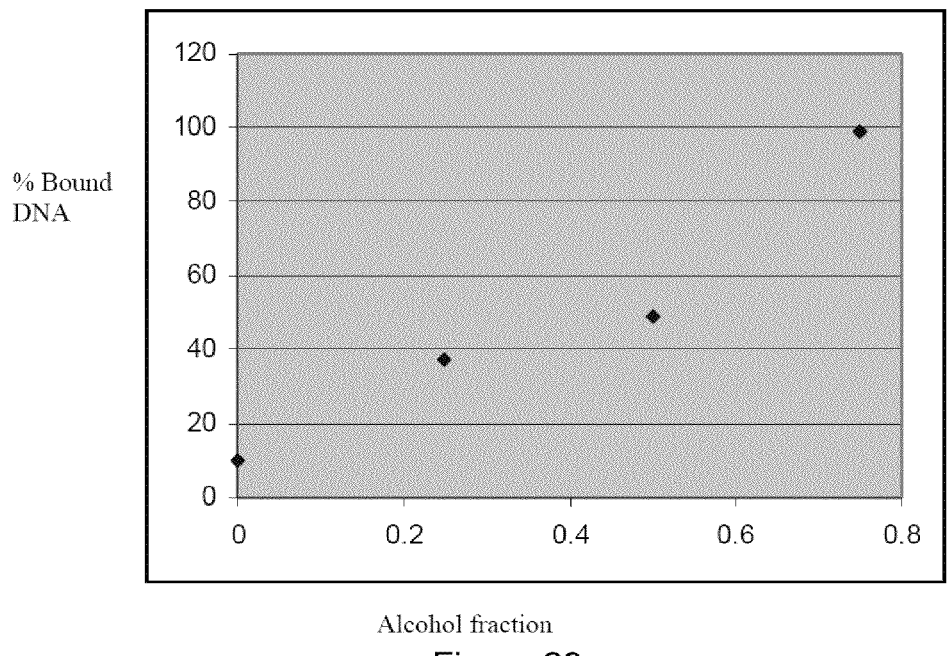
FIG. 29 is a graphical representation showing the release of the nucleic acid molecules from the magnetic particles.

Radiolabled DNA was used to determine the efficiency of binding to ferrite and the release of the nucleic acid molecules. Radiolabeled DNA with the magnetite suspension and three volumes of ethanol were mixed. The magnetite was pulled to the bottom of the tube using a magnet. The supernatant fluid was removed from the pellet and both fractions were counted in a scintillation counter. Binding was measured as a function of the fraction of ethanol in the mix. The results are shown in FIG. 29.

To determine the release efficiency, the bound DNA pellet is suspended in 100 μl of buffer as indicated in the table below, incubated for 10 minutes at 95° C., then collected on the magnet. The supernatant was separated from the pellet and both were counted.

| Buffer | Supernatant cpm | Pellet cpm | % Free |
|---|---|---|---|
| 500 mM Phosphate | 43,450 | 1925 | 96% |
| 50 mM Phosphate | 18,409 | 684 | 96% |
| 60 mM Citrate | 33,276 | 2164 | 94% |
| 100 mM Tris 0.2% SDS 1.5% Dextran sulfate | 911 | 35,878 | 3% |

The Tris buffer with SDS can be used for hybridization with magnetite bound DNA in order to allow for magnetic concentration of DNA or RNA near the sensor.

Rapid Movement of Particles Example

Microchips were fabricated with metal coils having line widths of one micron. A current was run through the coils to produce a magnetic field. A solution containing magnetic nano-particles was then spotted over the coils. The chip was placed under a microscope and current turned on through the coil. Within 10 seconds, clusters were congregating at the corners within the coil. Once the current was turned off the particles demagnetize and begin to diffuse back into solution.

Tissue Samples

Figure 30:
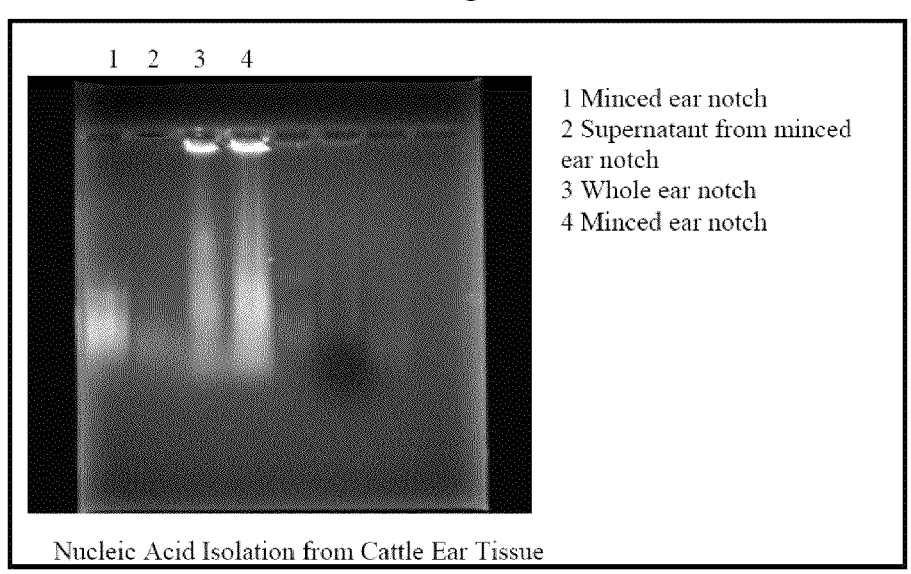
FIG. 30 demonstrates the nucleic acid molecule isolation obtained from using tissue from the ear of a cow.

As shown in FIG. 30, for diagnostic samples, an approach using tissue from the ear of a cow was evaluated. Ear tissue is often taken from cattle for evaluation and has skin, hair, large amounts of cartilage and is rich in blood. Ear plugs of about 3 mm in diameter were tested. A robust sample of about 1 microgram of nucleic acid molecules was isolated from an earplug using ultrasonication and 40 nm ferrite particles. The nucleic acid molecules were in the expected size range. Glass beads were not required for extraction from the tissue and subsequent treatment of an ear plug with bead beating did not result in additional nucleic acid molecule extraction. Sonication power and time settings were identical to those used in the previous examples.

Samples Contaminated with Soil

Figure 31:
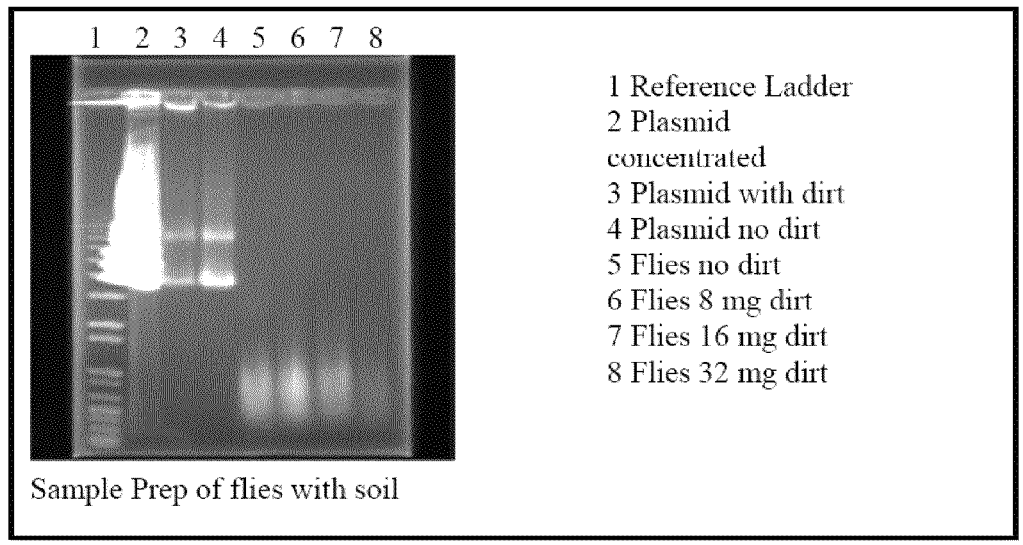
FIG. 31 demonstrates the nucleic acid molecule isolation obtained from using fruit flies contaminated with soil.

As shown in FIG. 31, to evaluate complex samples, bacterial and spore samples mixed with soil were processed. Soil is a complex medium which is known to inhibit PCR-based systems. Soil was added to samples containing six whole fruit flies. The flies are intended to represent insects that might be evaluated for carrying a disease like malaria. Up to 32 milligrams of the soil were added per milliliter of sample. The fruit flies were disrupted using ultrasonication in the presence of ferrite particles for two minutes. DNA and RNA were captured using ferrite particles with the addition of ethanol. The particles were collected magnetically, washed with buffer and ethanol to remove contaminants then concentrated with magnetics. The nucleic acid molecules were then eluted in hybridization buffer at 90° C. to denature the DNA component. Minimal loss was seen until the level of soil in the sample reached 32 milligrams per 100 micro liters (lane 8) where the solution becomes viscous and particle movement is difficult under the current test conditions. It is understood that by increasing the disrupting power, modifying the solution, or changing the disrupting particles size or characteristics results could be optimized for extremely contaminated samples.

Preparation of Magnetite Clusters

A first solution of ferric chloride (0.8M), ferrous chloride (0.4M) and hydrochloric acid (0.4M) was mixed and 0.2 micron filtered. A second solution was prepared with 72 ml of ammonium hydroxide (30%) with water to make 1 liter.

1 ml of the ferric/ferrous chloride solution was added with stirring to 20 ml of the ammonium hydroxide solution. Stirring was continued for 15 seconds. The solution (in a 20 ml vial) was placed on a strong magnet and allowed to stand for 1 minute, after which all the product was pulled to the bottom of the vial. The clear supernatant liquid was decanted, replaced with water, mixed, and placed near the magnet. Again the product was pulled to the bottom of the vial. This process was repeated three times to wash the product free from any residual ammonium and iron salts. The vial was then filled with 20 ml of water and ultra-sonicated for 5 minutes at 4 watts power. The suspension was then filtered through a 1 micron glass filter to give a stable suspension of magnetite particles that remain in suspension until pulled down by magnetic forces or centrifugation.

Example A

Three fruit flies were placed in each of two 1.5 ml Eppendorf tubes. One was loaded with 100 microliters of a mixture of 100 mM TRIS hydrochloride (pH 7.5), 1.5% dextran sulfate and 0.2% sodium dodecylsulfate (SDS). The other was loaded with 100 microliters of isopropyl alcohol and 10 microliters of 20% sodium dodecylsulfate. Both tubes were loaded with 10 microliters of 0.6% magnetite nanoparticles in water. Both tubes were sonicated at 20 kHz for 45 seconds (2 watts). Then 1 ml of isopropyl alcohol was added to the first tube and ½ ml of isopropyl alcohol was added to the second tube. The magnetic pellet was collected by a permanent magnet, the supernatant liquid decanted and 50 μl of 100 mM sodium phosphate was added to each tube, the pellet resuspended by repetitive pipetting, then incubated at 95 degrees C. for 2 minutes. The pellet was again collected on a magnet and the eluted DNA was run on a 1% agarose gel at 77 volts in TEA buffer. A DNA ladder was also run on the gel.

Figure 32:
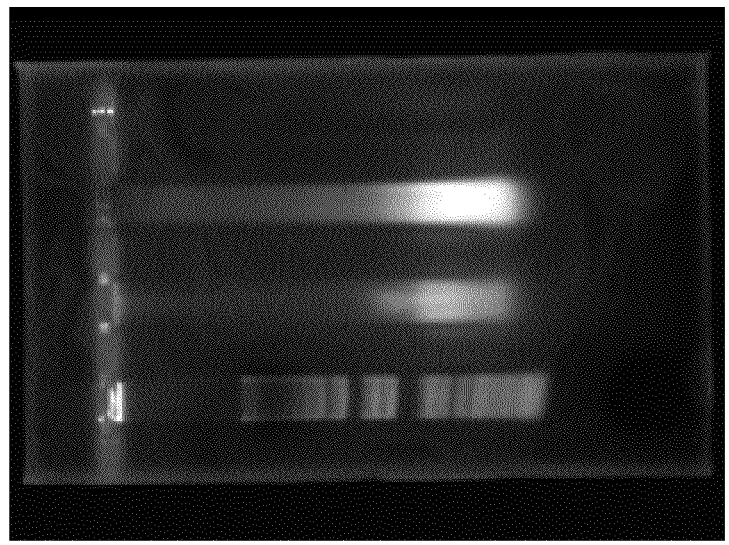
FIG. 32 demonstrates purified DNA recovered from fruit flies.

As shown in FIG. 32, the gel was stained with ethidium bromide and photographed with 302 nm excitation and a 610 nm filter over the camera. The purified DNA is clearly visible on the photograph. The top lane represents the second tube, the middle lane represents the first tube and the bottom lane represents a DNA ladder.

Example B

Figure 33:
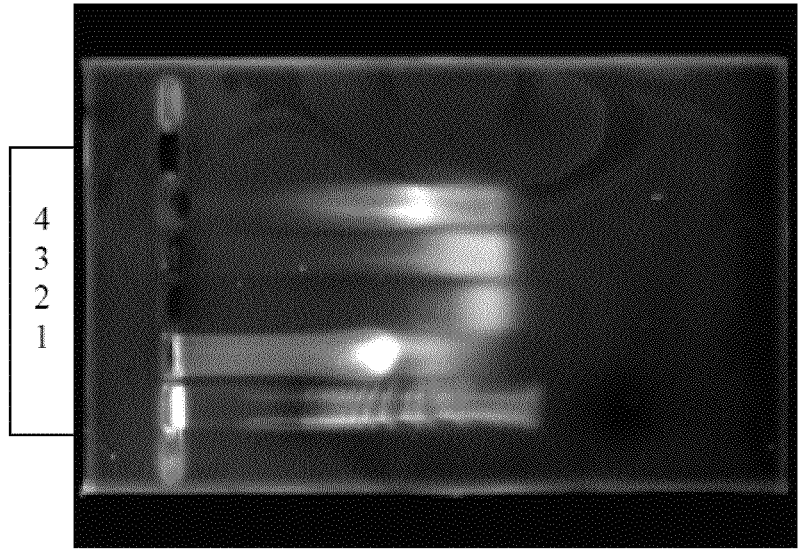
FIG. 33 demonstrates DNA recovered from fruit flies using various buffers.

Four tubes, each with three fruit flies, 100 microliters of buffer and 10 µl of 0.6% magnetite nanoparticles were sonicated for 30 seconds at 5 watts at 20 kHz. The DNA was collected, eluted, run on a gel, stained and photographed as in Example A and shown in FIG. 33. The four buffers were as follows:
1. 100 mM TRIS, 1.5% Dextran sulfate and 0.2% SDS
2. Isopropylalcohol (IPA)
3. 90% IPA, 1% dodecylbenzenesulfate, 9% water
4. 90% IPA, 1% polyacrylic acid sodium salt, 9% water Example 13

Figure 34:
FIG. 34 demonstrates the recovery of nucleic acid molecules from yeast, grass and blueberries.

Portions of yeast, grass and blueberries were sonicated in 100 mM TRIS, 1.5% Dextran sulfate and 0.2% SDS as in Example A. The purification, gel and photograph were as in Example A and are shown in FIG. 34.

Example C

Three 1.5 ml Eppendorf tubes each containing about 10 billion *E. coli* cells and 33 mg of glass beads (100 micron diameter) and 40 microliters of 0.5 molar sodium phosphate, pH 7.5 were sonicated for 15, 30 and 60 seconds at 40 kHz, 10% amplitude with a 4 mm sonic tip inserted into the tube. The purification, gel and photograph were done as in Example A and are shown in FIG. 35.

This example shows that longer sonication times do not change the size distribution, i.e., that steady state conditions apply.

Example D

Figure 36:
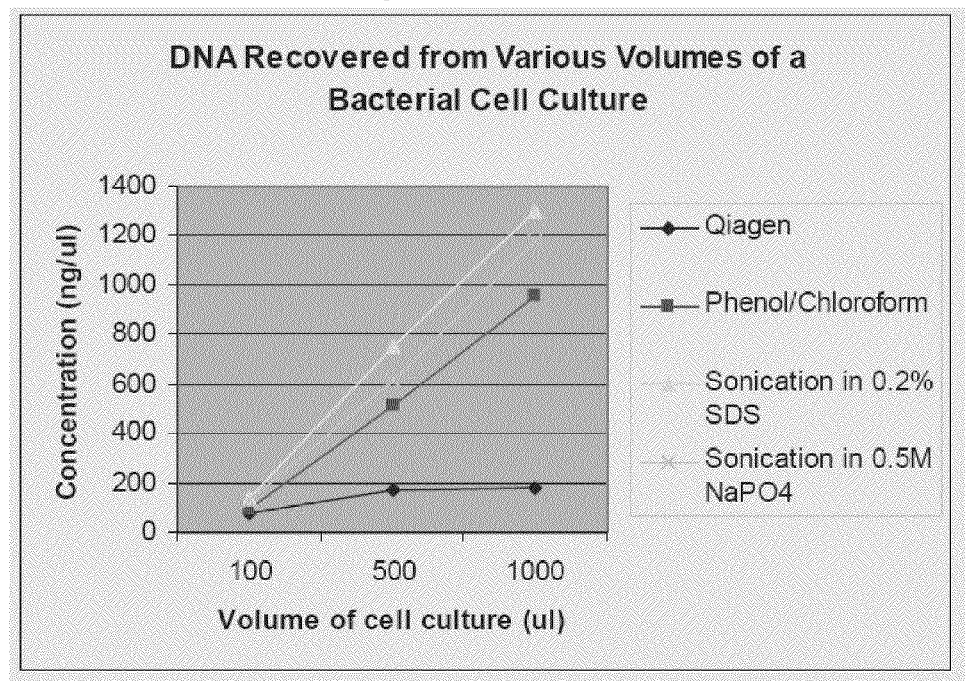
FIG. 36 is a graphical representation of DNA recovery from increasing volumes of a bacterial cell culture using the instant invention, the commercial Qiagen kit for DNA recovery and the textbook Phenol/Chloroform method.

In this example, DNA is recovered from increasing volumes of a bacterial cell culture using two standard methods— the commercial Qiagen kit for DNA recovery and the textbook Phenol/Chloroform method. These were compared to the method given in Example A, using 0.2% SDS and 0.5 M sodium phosphate as the buffer. The results are shown graphically in FIG. 36.

Figure 37:
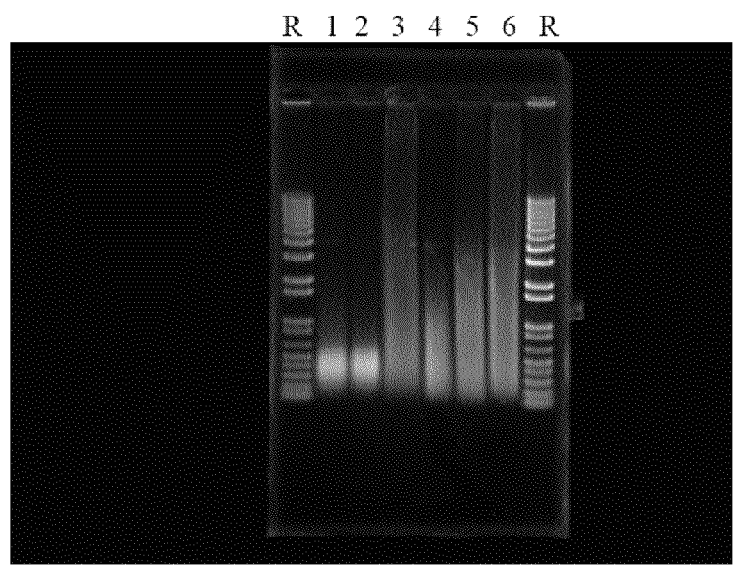
FIG. 37 demonstrates the effectiveness of high ionic strength buffer in protecting nucleic acid molecules during sonication.

The graph shows that the method of this invention is superior to both the Qiagen kit and the phenol/chloroform method Protective Buffer Example In this example a comparison of protective buffers for DNA shearing by ultrasonication are shown in FIG. 37.

5 ul G1 plasmid DNA solution containing 5 ug of DNA were mixed with 50 ul buffer with 44 mg of zirconia beads of approximately 100 micron size in a 1.5 ml eppendorf tube. The tube was inserted into the socket of a Branson SLPt 40 kHz ultrasonicator. The sonicator was run at 50% amplitude for 12 minutes with a pulsed cycle of 10" on and 20" off. After sonication, a 20 ul portion of the mixture was eletrophorized on a 1% agarose gel at 100 volts in TAE buffer. All buffers were adjusted to a pH between 7 and 8. A DNA ladder was run on both sides of the sample lanes. The lanes contained:
Lane 1. TE (Tris-(hydroxymethyl)aminomethane) with EDTA (ethylene diamine tetra-acetic acid)
Lane 2. 10 mM Tris-(hydroxymethyl)aminomethane
Lane 3. 500 mM sodium phosphate
Lane 4. 50 mM sodium phosphate
Lane 5. 60 mM sodium citrate
Lane 6. 3% sodium chloride This example shows that high ionic strength buffers, such as metal salts are effective in protecting the DNA during sonication. The buffer allows for larger DNA fragments in a steady state sonication. Lower ionic strength buffers such as Tris-hydroxymethyl aminomethane are less protective and yield smaller DNA fragments suitable for particular applications.

In one embodiment, the size stabilizer is a protective high ionic strength buffer including soluble salts from cations including the Group1 and Group2 metals of the periodic table with anions from Group 7 of the periodic table as well as more complex anions exemplified by sulfates, phosphates, and acetates. In another embodiment the buffer is capable of being stable and soluble at pH values between 7 and 8. The soluble concentration of the buffers is preferably greater than 1%, and most preferably greater than 5%.

Surfactant Examples

Two fruit flies were placed in each of 3 eppendorf tubes containing 25 µl of 100 micron glass beads from Biospec Products. To the first tube, 100 microliters of water was added. To the second tube, 100 microliters of 1% sodium dodecylsulfate was added. To the third tube, 100 microliters of 1% sodium dodecylbenzenesulfate was added. All three tubes were sonicated for 2 minutes on power level 2 on a Branson Sonifier 150, placing the tube into the threaded orifice of the ultrasonic converter where the tips are normally threaded into the converter. The power meter showed an initial reading of about 8 watts which dropped during the 30 seconds to about 4 watts, which level continued during the remainder of the sonication time. After sonication, 20 microliters of the fluid above the glass beads was removed and placed in the wells of an agarose electrophoresis gel, made with TAE buffer. A DNA ladder was included in the first lane to determine the size of the sonicated DNA fragments. After electrophoresis at 70 volts for 90 minutes, the gel was soaked with gentle agitation with an ethidium bromide solution. Then a black light photograph of the gel was taken, as shown in FIG. 38.

Figure 38:
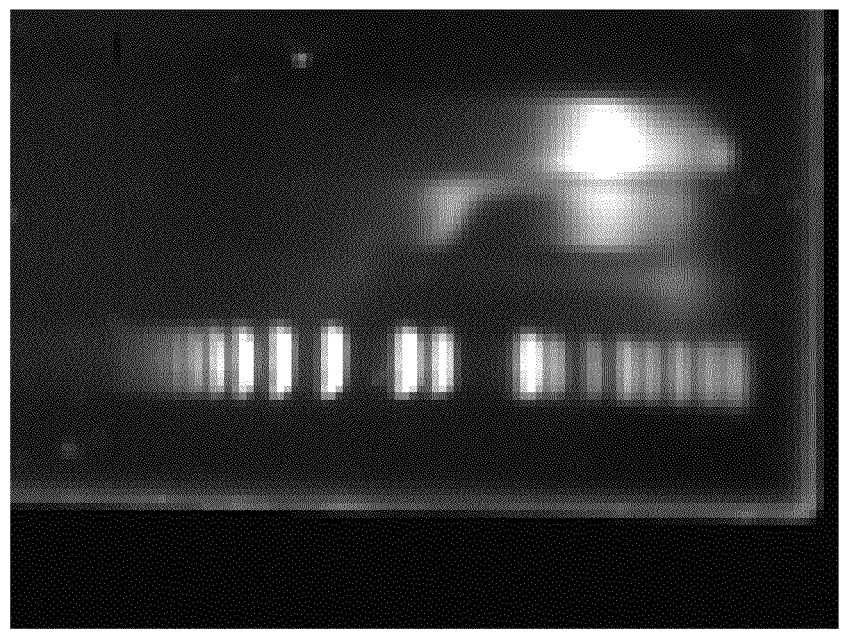
FIG. 38 demonstrates that sonication in the presence of a selected size stabilizer can provide a high yield of DNA in a limited size range.

Referring to FIG. 38, the first lane above the DNA ladder shows the water sonication result. A low yield of DNA is seen, and the fragments are smaller than 400 base pairs. The second lane above the ladder shows the sodium dodecyl sulfate sonication result. The yield of DNA is much higher, and the fragment sizes range from 300 to 2000 base pairs in size. The third lane above the ladder shows the sodium dodecylbenzenesulfate result. Again, the yield of DNA is high, evidenced by the bright spot on the photograph, and the size range is from 300 to 1000 base pairs. This example shows that sonication in the presence of a selected surfactant can provide a high yield of DNA in a limited size range from a live source such as fruit flies.

While the invention has been described with reference to particular embodiments, it will be understood by those skilled in the art that various changes may be made and equivalents may be substituted for elements thereof without departing from the scope of the invention. In addition, many modifications may be made to adapt a particular situation or material to the teachings of the invention without departing from the scope of the invention.

Therefore, it is intended that the invention not be limited to the particular embodiments disclosed as the best mode contemplated for carrying out this invention, but that the invention will include all embodiments falling within the scope and spirit of the appended claims.

The invention claimed is:

1. A method for sample preparation comprising the steps of:
   delivering a biological sample to a disposable cartridge with a cylindrical reservoir insert having
      a plurality of chambers including a first chamber with a first port that terminates at an outer wall of the cylindrical reservoir insert, the cylindrical reservoir insert being rotatable about an axis of rotation and the outer wall being parallel to the axis of rotation and defining a perimeter of the cylindrical reservoir insert, the plurality of chambers being within the perimeter of the outer wall,
      a through-channel that extends along a bottom surface of the cylindrical reservoir insert, the through-channel having a second port and a third port at respective ends of the through-channel and each terminating at the outer wall;
   mixing said biological sample in a first volume of buffer in said first chamber; and
   disrupting said sample in the presence of a size stabilizer to obtain nucleic acid molecules;
   aligning the first port with a plunger;
   actuating the plunger to withdraw the nucleic acid molecules out of the disposable cartridge and into the plunger;
   aligning the second port with the plunger by rotating the cylindrical reservoir insert about the axis of rotation;
   actuating the plunger to inject the nucleic acid molecules out of the plunger and into the through-channel.

2. The method of claim 1 further comprising the step of passing said biological sample through a filter prior to delivery to said first chamber.

3. The method of claim 1 further comprising the step of attaching magnetic nanoparticles to said nucleic acid molecules.

4. The method of claim 3 further comprising the step of applying a magnetic field to concentrate said magnetic nanoparticles and any nucleic acid molecules attached thereto to a first portion of a first reservoir in said disposable cartridge.

5. The method of claim 4 further comprising the step of eluting the nucleic acid molecules from the magnetic nanoparticles with a second volume of buffer that is smaller than the first volume of buffer to provide a first sample of the nucleic acid molecules.

6. The method of claim 5 further comprising the step of drawing the first sample from the first portion of a first reservoir, through a delivery port and delivering the first sample to a second reservoir in said disposable cartridge.

7. The method of claim 5 further comprising the step of applying a magnetic field to hold said magnetic nanoparticles and any nucleic acid molecules attached thereto.

8. The method of claim 7 further comprising the step of washing said first sample with a rinse solution to wash away any non-bound objects, wherein said magnetic field is sufficient to hold said magnetic nanoparticles and any nucleic acid molecules attached thereto in place.

9. The method of claim 8 further comprising the step of releasing said nucleic acid molecules from said magnetic nanoparticles by eluting with an elution buffer.

10. The method of claim 8 wherein said rinse solution is ethanol.

11. The method of claim 9 wherein said elution buffer is a solution of 2-Amino-2-hydroxymethyl-propane-1,3-diol in water.

12. The method of claim 1 further comprising the steps of:
   attaching magnetic nanoparticles to said nucleic acid molecules;
   applying a magnetic field strong enough to manipulate said magnetic nanoparticles to concentrate the magnetic nanoparticles and the attached nucleic acid molecules;
   providing a rinse solution to wash away any sample unbound to said magnetic nanoparticles.

13. The method of claim 1, wherein the cylindrical reservoir insert has a second chamber with an access port that terminates at the outer wall of the cylindrical reservoir insert, the method further comprising the steps of:
   rotating the disposable cartridge to align the access port with the plunger;
   actuating the plunger to inject the nucleic acid molecules into the second chamber.

14. A method for sample preparation comprising the steps of:
   delivering a biological sample to a disposable cartridge with a cylindrical reservoir insert having:
      a plurality of chambers within a perimeter of an outer wall of the cylindrical reservoir insert and a plurality of ports, each port corresponding to a chamber of the plurality of chambers, each port terminating at the outer wall, the cylindrical reservoir insert being rotatable about an axis of rotation and the outer wall being parallel to the axis of rotation;
      a through-channel within the perimeter of the outer wall that extends along a bottom surface of the cylindrical reservoir insert and perpendicular to the axis of rotation, the through-channel having two access ports, each at respective ends of the through-channel and each access port terminating at the outer wall;
      a cartridge body rotatably housing the cylindrical reservoir insert and having a syringe molding that is configured to selectively align with a select port of the plurality of ports;
   disrupting said sample to obtain nucleic acid molecules;
   aligning a first port of the plurality of ports with the syringe molding;
   actuating a plunger that is fluidly connected to the syringe molding to withdraw the nucleic acid molecules out of the disposable cartridge and into the plunger;
   aligning one of the two access ports with the syringe molding by rotating the cylindrical reservoir insert about the axis of rotation;
   actuating the plunger to inject the nucleic acid molecules out of the plunger and into the through-channel.

15. The method as recited in claim 14, wherein each port of the plurality of ports is a fixed distance from a bottom edge of the cylindrical reservoir insert such that each port of the plurality of ports may be selectively aligned with the syringe molding.

16. The method as recited in claim 14, wherein the cylindrical reservoir insert comprises a relief port for each chamber in the plurality of chambers, the method comprising permitting air to pass through the relief port to prevent pressure differentials from forming within each chamber in the plurality of chambers when the plunger is actuated.

17. The method as recited in claim 14, wherein the cylindrical reservoir insert comprises a secondary through-channel within the perimeter of the outer wall that extends along the bottom surface of the cylindrical reservoir insert and perpendicular to the axis of rotation, the secondary through-channel having two secondary access ports, each at respective ends of the secondary through-channel and each secondary access port terminating at the outer wall, the method further comprising actuating the plunger to inject fluid through one of the secondary access ports and into the secondary through-channel.

18. The method as recited in claim 17, wherein the through-channel and the secondary-through channel are fluidly isolated so as to prevent contamination of the through-channel and the secondary-through channel.

19. The method as recited in claim 14, further comprising actuating the plunger to pass fluid out of the cylindrical reservoir insert and into a reaction chamber that is disposed on an external surface of the cartridge body.

* * * * *